United States Patent
Langley et al.

(10) Patent No.: US 7,994,136 B1
(45) Date of Patent: Aug. 9, 2011

(54) METALLOPROTEINASE INHIBITOR

(75) Inventors: Keith E. Langley, Newbury Park, CA (US); Yves A. DeClerck, Los Angeles, CA (US); Thomas C. Boone, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 07/355,027

(22) Filed: May 19, 1989

(51) Int. Cl.
*A61K 38/17* (2006.01)
*A61K 38/57* (2006.01)
*A61K 38/43* (2006.01)

(52) U.S. Cl. ...... 514/20.1; 514/1.1; 514/21.3; 514/21.1; 435/69.2; 435/69.7; 530/324; 530/400; 530/407; 530/350

(58) Field of Classification Search .................. 530/350; 514/12; 435/69.2

See application file for complete search history.

(56) References Cited

PUBLICATIONS

Docherty et al "Sequence of Human Tissue Inhibitor of Metalloproteinases and its Identity to Erythroid-Potentiating Activity" Nature v.318, 66-69 (Nov. 1985).*
Murray et al "Purification and Partial Amino Acid Sequence of a Bovine Cartilage-Derived Collagenase Inhibitor" J. Biol. Chem. v.261 (9) pp. 4154-4159. (Mar. 1986).*
Bethesda Research Laboratories 1985 Catalog. p. 62.*

* cited by examiner

*Primary Examiner* — Lorraine Spector
(74) *Attorney, Agent, or Firm* — James E. Klaniecki

(57) ABSTRACT

A novel metalloproteinase inhibitor, analogs thereof, polynucleotides encoding the same, and methods of production, are disclosed. Pharmaceutical compositions and methods of treating disorders caused by excessive amounts of metalloproteinase are also disclosed.

15 Claims, 13 Drawing Sheets

```
att ccg gct tct atg gag cac tcg gga cca ggt ccg cgg cgc gcg cac tcg ctc
gct cgc cgc ccc cca gcc agc tct cgc ttc cgc gcc gcc agc cgc gcc ccg cgc
ctc ctc gct gca ccc cgc gac cta gag cca aga aag ttt gtg tgg cga gtg agg
gcc gga gag gag agc gcg ccc gcg gag tgc cgt cca gac cag cgc ggc ccc ggc
gga gag ggg agc gcc ccg agc cca ggc ggc ggc tag ccc gag tcc gcg acc
                           -26                              -20
                           Met Gly Ala Ala Ala Arg Ser Leu Pro Leu Ala Phe
ccc gcc cct ccg ccg gcc atg ggc gcc gcc gcc cgc agc ctg ccg ctc gcg ttc
               -10                                        -1  1
Cys Leu Leu Leu Leu Gly Thr Leu Leu Pro Arg Ala Asp Ala Cys Ser Cys Ser
tgc ctc ctg ctg ctg ggg acg ctg ctc ccc cgg gcc gac gcc tgc agc tgc tcc
                    10                                        20
Pro Val His Pro Gln Gln Ala Phe Cys Asn Ala Asp Ile Val Ile Arg Ala Lys
ccg gtg cac ccg caa cag gcg ttt tgc aat gca gac ata gtg atc agg gcc aaa
                         30                                           40
Ala Val Asn Lys Lys Glu Val Asp Ser Gly Asn Asp Ile Tyr Gly Asn Pro Ile
gca gtc aat aag aag gag gtg gac tct ggc aac gac atc tac ggc aac ccc atc
                              50
Lys Arg Ile Gln Tyr Glu Ile Lys Gln Ile Lys Met Phe Lys Gly Pro Asp Gln
aag cgg att cag tat gag atc aag cag ata aag atg ttc aag gga cct gat cag
     60                                        70
Asp Ile Glu Phe Ile Tyr Thr Ala Pro Ala Ala Ala VAl Cys Gly VAl Ser Leu
gac ata gag ttt atc tac aca gcc ccc gcc gct gcc gtg tgt ggg gtc tcg ctg
               80                                          90
Asp Ile Gly Gly Lys Lys Glu Tyr Leu Ile Ala Gly Lys Ala Glu Gly Asn Gly
gac att gga gga aag aag gag tat ctc att gca ggg aag gcc gag ggg aat ggc
                    100                                         110
Asn Met His Ile Thr Leu Cys Asp Phe Ile Val Pro Trp Asp Thr Leu Ser Ala
aat atg cat atc acc ctc tgt gac ttc atc gtg ccc tgg gac acc ctg agt gcc
                         120                                          130
Thr Gln Lys Lys Ser Leu Asn His Arg Tyr Gln Met Gly Cys Glu Cys Lys Ile
acc cag aag aag agc ctg aac cac agg tac cag atg ggc tgt gag tgc aag atc
                              140
Thr Arg Cys Pro Met Ile Pro Cys Tyr Ile Ser Ser Pro Asp Glu Cys Leu Trp
act cga tgc ccc atg atc cca tgc tac atc tcc tct ccg gac gag tgc ctc tgg
     150                                        160
Met Asp Trp Val Thr Glu Lys Asn Ile Asn Gly His Gln Ala Lys Phe Phe Ala
atg gac tgg gtc acg gag aag aac atc aac gga cac cag gcc aag ttc ttc gcc
               170                                          180
Cys Ile Lys Arg Ser Asp Gly Ser Cys Ala Trp Tyr Arg Gly Ala Ala Pro Pro
tgc atc aag aga agc gac ggc tcc tgc gcc tgg tac cgc gga gca gca ccc ccc
                    190            194
Lys Gln Glu Phe Leu Asp Ile Glu Asp Pro (SEQ ID NO: 7)
aag cag gag ttt ctg gac atc gag gac ccg taa gca cac cag gac tcc tgg
ggc caa ttg aca gtg tcc aag agt tca gac tgg tcc agc tcc gac atc cct tcc
tgg aca cag cat gaa taa a (SEQ ID NO: 6)
```

*Fig. 1*

```
att ccg gcc cgt ccc cca ccc cgc cgc ccc gcc cgg cga att gcg ccc cgc
gcc cct ccc ctc gcg ccc ccg aga caa aga gga gag aaa gtt tgc gcg gcc gag
cgg ggc agg tga gga ggg tga gcc gcg cgg gag ggg ccc gcc tcg gcc ccg gct
cag ccc ccg ccc gcg ccc cca gcc cgc cgc cgc gag cag cgc ccg gac ccc cca
                                                  -26
                                                      Met Gly Ala Ala Ala Arg
gcg gcg gcc ccc gcc cgc cca gcc ccc cgg ccc gcc atg ggc gcc gcg gcc cgc
-20                                                -10
Thr Leu Arg Leu Ala Leu Gly Leu Leu Leu Leu Ala Thr Leu Leu Arg Pro Ala
acc ctg cgg ctg gcg ctc ggc ctc ctg ctg ctg gcg acg ctg ctt cgc ccg gcc
   -1  1                                         10
Asp Ala Cys Ser Cys Ser Pro Val His Pro Gln Gln Ala Phe Cys Asn Ala Asp
gac gcc tgc agc tgc tcc ccg gtg cac ccg caa cag gcg ttt tgc aat gca gat
              20                                 30
Val Val Ile Arg Ala Lys Ala Val Ser Glu Lys Glu Val Asp Ser Gly Asn Asp
gta gtg atc agg gcc aaa gcg gtc agt gag aag gaa gtg gac tct gga aac gac
                 40                                 50
Ile Tyr Gly Asn Pro Ile Lys Arg Ile Gln Tyr Glu Ile Lys Gln Ile Lys Met
att tat ggc aac cct atc aag agg atc cag tat gag atc aag cag ata aag atg
                    60                                 70
Phe Lys Gly Pro Glu Lys Asp Ile Glu Phe Ile Tyr Thr Ala Pro Ser Ser Ala
ttc aaa ggg cct gag aag gat ata gag ttt atc tac acg gcc ccc tcc tcg gca
                       80
Val Cys Gly Val Ser Leu Asp Val Gly Gly Lsy Lsy Glu Tyr Leu Ile Ala Gly
gtg tgt ggg gtc tcg ctg gac gtt gga gga aag aag gaa tat ctc att gca gga
  90                                  100
Lys Ala Glu Gly Asp Gly Lys Met His Ile Thr Leu Cys Asp Phe Ile Val Pro
aag gcc gag ggg gac ggc aag atg cac atc acc ctc tgt gac ttc atc gtg ccc
          110                                 120
Trp Asp Thr Leu Ser Thr Thr Gln Lys Lys Ser Leu Asn His Arg Tyr Gln Met
tgg gac acc ctg agc acc acc cag aag aag agc ctg aac cac agg tac cag atg
                130                                 140
Gly Cys Glu Cys Lys Ile Thr Arg Cys Pro Met Ile Pro Cys Tyr Ile Ser Ser
ggc tgc gag tgc aag atc acg cgc tgc ccc atg atc ccg tgc tac atc tcc tcc
                   150                                 160
Pro Asp Glu Cys Leu Trp Met Asp Trp Val Thr Glu Lys Asn Ile Asn Gly His
ccg gac gag tgc ctc tgg atg gac tgg gtc aca gag aag aac atc aac ggg cac
                       170
Gln Ala Lys Phe Phe Ala Cys Ile Lys Arg Ser Asp Gly Ser Cys Ala Trp Tyr
cag gcc aag ttc ttc gcc tgc atc aag aga agt gac ggc tcc tgt gcg tgg tac
       180                                 190         194
Arg Gly Ala Ala Pro Pro Lys Gln Glu Phe Leu Asp Ile Glu Asp Pro (SEQ ID NO: 9)
cgc ggc gcg gcg ccc ccc aag cag gag ttt ctc gac atc gag gac cca taa gca ggc ctc caa cgc ccc tgt ggc caa ctg caa aaa aag cct cca agg gtt tcg act ggt cca gct ctg aca tcc ctt cct gga aac agc atg aat aaa aca ctc atc ccc gga att c (SEQ ID NO: 8)
```

*Fig. 2*

```
        10         20         30         40         50         60
CTAGAAAAAA CCAAGGAGGT AATAAATAAT GTGTTCTTGT TCTCCTGTAC ACCCTCAACA
TTTTTT     GGTTCCTCCA TTATTTATTA CACAAGAACA AGAGGACATG TGGGAGTTGT 70         80         90        100        110        120
AGCTTTTTGT AACGCTGATG TAGTTATCCG TGCAAAAGCT GTTTCTGAAA AAGAAGTTGA
TCGAAAAACA TTGCGACTAC ATCAATAGGC ACGTTTTCGA CAAAGACTTT TTCTTCAACT 130        140        150        160
TTCTGGTAAC GACATCTACG GTAACCCGAT CAAAAG      (SEQ ID NO: 35)
AAGACCATTG CTGTAGATGC CATTGGGCTA GTTTTCCTAG  (SEQ ID NO: 36)
```

*Fig. 9*

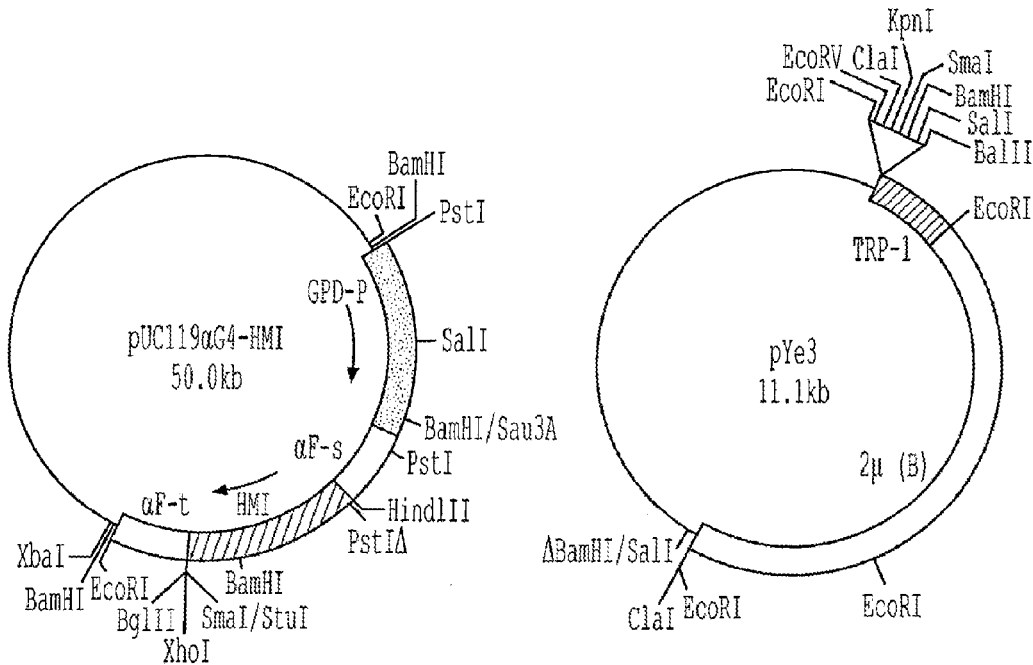
*Fig. 10A*  *Fig. 10B*
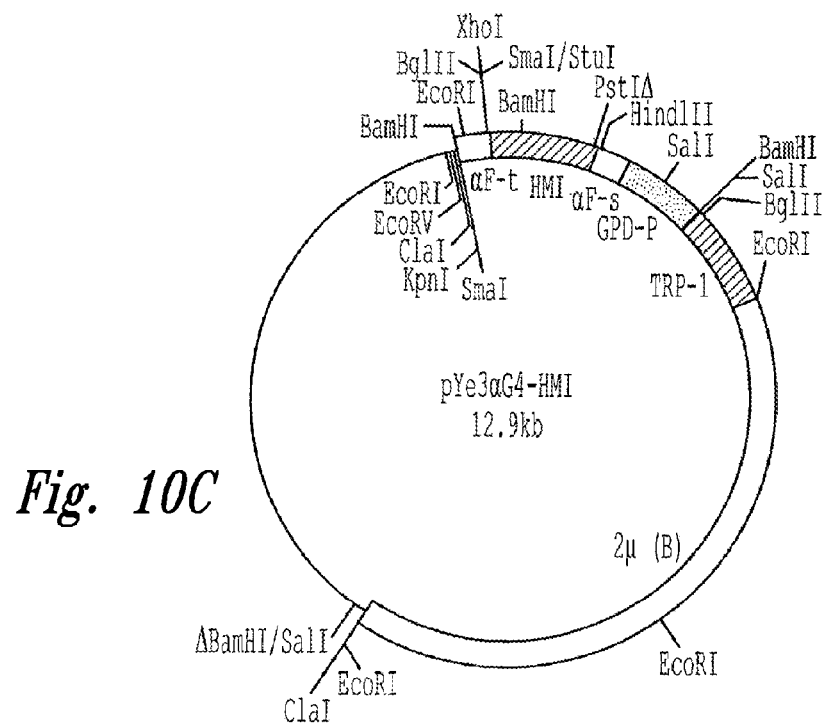
*Fig. 10C*

METALLOPROTEINASE INHIBITOR

The present invention relates in general to metalloproteinase inhibitors and to polynucleotides encoding such factors. In particular, the invention relates to a novel mammalian metalloproteinase inhibitor (MI), to fragments and polypeptide analogs thereof and to polynucleotides encoding the same.

BACKGROUND OF THE INVENTION

Connective tissues are maintained in dynamic equilibrium by the opposing effects of cellular connective tissue synthesis and extracellular degradation. The extracellular connective tissue matrix consists predominantly of collagens, with proteoglycans, fibronectin, laminin and other minor components making up the remainder.

Degradation of the matrix is brought about by the release of neutral metalloproteinases from resident connective tissue cells and invading inflammatory cells that are capable of degrading at physiological pH most of the matrix macromolecules. The proteinases include the mammalian tissue collagenases, gelatinases, and proteoglycanases; leukocyte collagenase and gelatinase [Murphy et al. Biochem. J. 283, 289-221 (1982); Hibbs et al., J. Biol. Chem. 260, 2493-2500 (1985)]; macrophage collagenase and elastase [Werb et al. J. Exp. Med. 142, 346-360 (1975); Banda et al., Biochem. J. 193, 589-605 (1981)]; and tumour collagenases [Liotta et al., Proc. Natl. Acad. Sci. USA 76 2268-2272 (1979); Liotta et al., Biochem. Biophys. Res. Commun. 98, 124-198 (1981); and Salo et al., J. Biol. Chem. 258, 3058-3063 (1983)]. For a general review of collagenases and their role in normal and pathological connective tissue turnover see *Collagenase in Normal and Pathological Connective Tissues*, David E. Woolley and John M. Evanson, eds., John Wiley & Sons Ltd. (1988).

There are over five different collagen types (I, II, III, IV, V, etc.) which are differently distributed among tissues. There is considerable homology and structural similarity among the various collagen types. Particular collagenases are specific for particular collagen types. With regard to inhibition of collagenases and other matrix-degrading metalloproteinases, it is possible that, depending on the actual enzymes, substrates, and inhibitory mechanisms, an inhibitor could act on just one, on several, or on all collagenases and metalloproteinases.

The underlying basis of degradative diseases of connective tissue points to the matrix-specific metalloproteinases as having a fundamental role in the aetiology of these diseases. Such diseases include dystrophic epidermolysis bullosa; rheumatoid arthritis; corneal, epidermal or gastric ulceration; peridontal disease; emphysema; bone disease; and tumor metastasis or invasion, and are discussed in more detail under the section Detailed Description of the Invention.

Most studies on connective tissue degradation and diseases involving such degradation have limited the measurement of metalloproteinases to collagenase (the most widely studied of this group of metalloproteinases). It is understood however, that the simultaneous effects of collagenase and the other matrix-degrading metalloproteinases will exacerbate the degradation of the connective tissue over that achieved by collagenase alone.

Specific natural inhibitors of collagenase were discovered in crude medium from cultured connective tissues. A metalloproteinase inhibitor known as TIMP (tissue inhibitor of metalloproteinases) has been studied with regard to physicochemical properties and the biochemistry of its interaction with collagenase [Murphy et al., J. Biochem. 195, 167-170 (1981); Cawston et al., J. Biochem. 211, 313-318 (1983); Stricklin et al. J. Biol. Chem. 258, 12252-12258 (1983)], and its gene has been isolated [Docherty et al. Nature 318, 65-69 (1985); Carmichael et al., Proc. Natl. Acad. Sci. USA 83, 2407-2411 (1986)]. In an in vitro cell culture model of tumor cell migration through a natural basement membrane, TIMP was able to arrest migration of a collagenase-secreting tumor cell line [Thorgeirsson et al., J. Natl. Canc. Inst. 69, 1049-1054 (1982)]. In vivo mouse lung colonization by murine B16-F10 melanoma cells was inhibited by injections of TIMP [Schultz et al., Cancer Research 48, 5539-5545 (1988)]. European patent application 189784 also relates to TIMP.

McCartney et al. [Eur. J. Biochem. 130, 79-83 (1983)] reported the purification of a metalloproteinase inhibitor from human leukocytes.

DeClerck et al. [Cancer Research 46, 3580-3586 (1986)] described the presence of two inhibitors of collagenase in conditioned medium from bovine aortic endothelial cells.

Murray et al. [J. Biol. Chem. 261, 4154-4159 (1986)] reported the purification and partial amino acid sequence of a bovine cartilage-derived collagenase inhibitor. The amino-terminal amino acid sequence of bovine MI of the subject invention is very similar to that reported by Murray et al. for the bovine cartilage-derived collagenase inhibitor (94% homology over first 38 residues), and the amino acid compositions are similar also. Murray et al. (J. Biol. Chem., supra) pointed out that the bovine cartilage-derived inhibitor had greater than 65% homology to human TIMP over the first 23 residues and that the amino-terminal sequences were "quite similar." Until the present work, no additional molecules related to or homologous to TIMP had ever been isolated from the same species from which a TIMP had been isolated. In the present work, two metalloproteinase inhibitors have been isolated and purified, and extensively characterized, from the same species (bovine) and indeed from the same cell conditioned medium. It is therefore clear that although they are related, as indicated, they cannot both be the bovine homolog of TIMP. One of them (peak II-derived), also as indicated, is probably bovine TIMP. The other (peak I-derived) must consequently be a new and additional molecule. Based on this discovery, it is apparent, for the first time, that there is a homologous inhibitor additional to TIMP encoded by the human genome. This human gene, i.e., the human MI gene, is set forth in Example 3.

To the extent that metalloproteinase inhibitors such as those described herein may prove to be therapeutically significant and hence need to be available in commercial scale quantities, isolation from cultures of naturally-occurring cells is unlikely to provide an adequate source of materials.

SUMMARY OF THE INVENTION

According to the present invention, a novel metalloproteinase inhibitor (MI), as well as analogs of MI, are provided. Also provided are DNA sequences coding for all or part of MI, vectors containing such DNA sequences, and host cells transformed or transfected with such vectors. Also comprehended by the invention are methods of producing recombinant MI, and methods of treating disorders. Additionally, pharmaceutical compositions including MI and antibodies specifically binding MI are provided.

BRIEF DESCRIPTION OF THE DRAWINGS

Note that in all Figures showing SDS-PAGE, numbered marks at the left represent migration positions of standards having molecular weights of $10^3$ times the indicated numbers. These markers were phosphorylase b ($M_r$ of 97,400), bovine serum albumin (BSA; $M_r$ of 66,200), ovalbumin ($M_r$ of 42,700) carbonic anhydrase ($M_r$ of 31,000), soybean trypsin inhibitor ($M_r$ of 21,500), and lysozyme ($M_r$ of 14,400). The standards were always reduced, even when some other samples run on the same gel were unreduced.

FIG. 1 shows the cDNA sequence and amino acid sequence of bovine metalloproteinase inhibitor.

FIG. 2 shows the cDNA sequence and amino acid sequence of human metalloproteinase inhibitor.

FIG. 9 shows a synthetic DNA fragment constructed for use in the expression of recombinant human metalloproteinase inhibitor in *E. coli*, containing a ribosome binding site, an initiation methionine codon, and codons for the first 42 amino acids of the mature protein.

FIG. 10 shows vectors used for expression of recombinant human metalloproteinase inhibitor in yeast.

Figure 3:
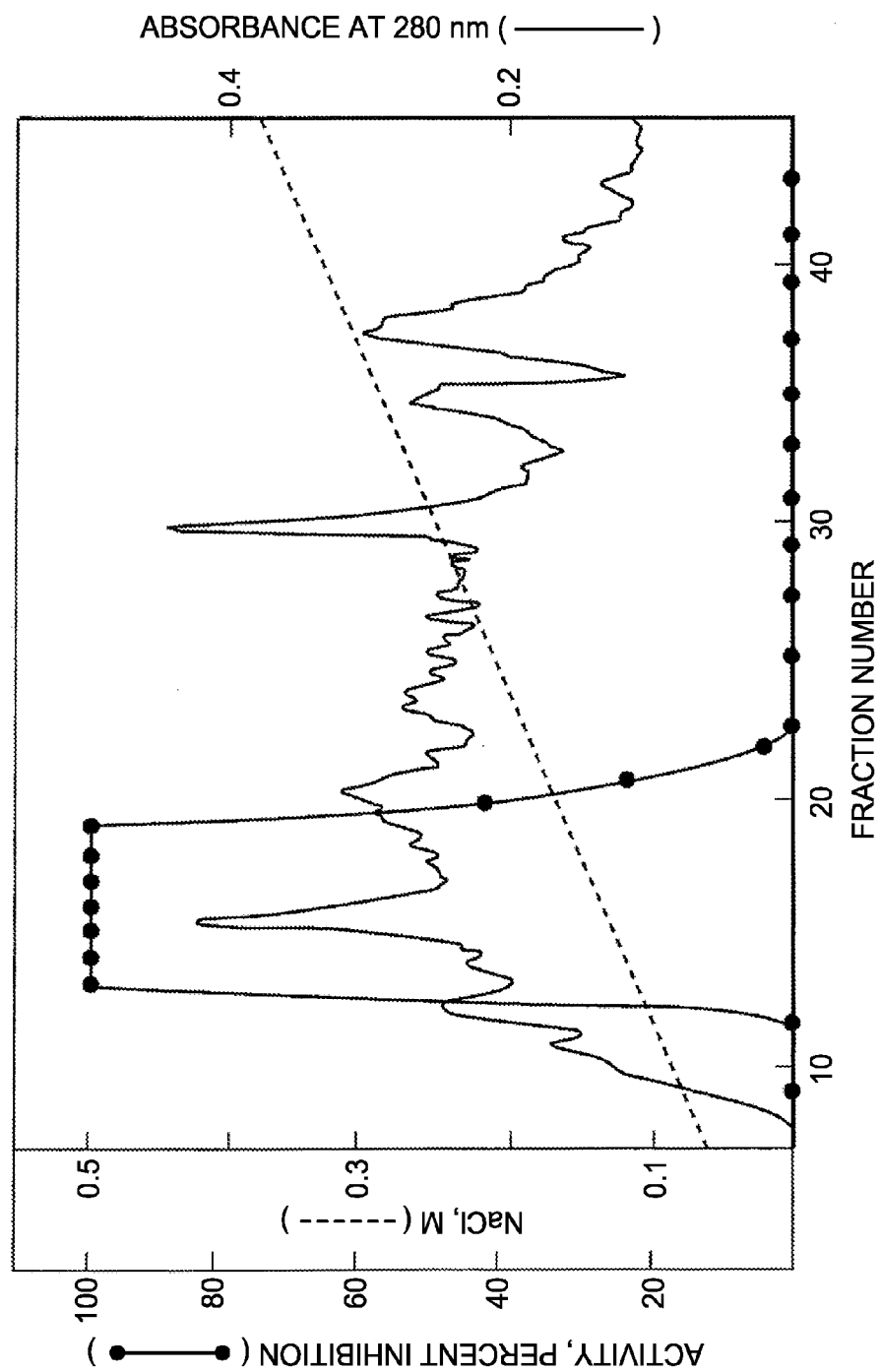
FIG. 3 shows anion exchange chromatography used in purification of bovine peak I-derived metalloproteinase inhibitor (MI).

Numerous aspects and advantages of the invention will be apparent to those skilled in the art upon consideration of the following detailed description which provides illustrations of the practice of the invention in its presently preferred embodiments.

DETAILED DESCRIPTION OF THE INVENTION

According to the present invention, a novel protein metalloproteinase inhibitor (MI) and DNA sequences coding for all or part of such MI are provided. Such sequences include: the incorporation of codons "preferred" for expression by selected nonmammalian hosts; the provision of sites for cleavage by restriction endonuclease enzymes; and the provision of additional initial, terminal or intermediate DNA sequences which facilitate construction of readily expressed vectors. The present invention also provides DNA sequences coding for polypeptide analogs or derivatives of MI which differ from naturally-occurring forms in terms of the identity or location of one or more amino acid residues (i.e., deletion analogs containing less than all of the residues specified for MI; substitution analogs, wherein one or more residues specified are replaced by other residues; and addition analogs wherein one or more amino acid residues is added to a terminal or medial portion of the polypeptide) and which share some or all the properties of naturally-occurring forms.

Novel DNA sequences of the invention include sequences useful in securing expression in procaryotic or eucaryotic host cells of polypeptide products having at least a part of the primary structural conformation and one or more of the biological properties of naturally-occurring MI. DNA sequences of the invention specifically comprise: (a) the DNA sequence set forth in FIG. 1 or FIG. 2 or their complementary strands; (b) a DNA sequence which hybridizes (under hybridization conditions disclosed in Example 3) or more stringent conditions to the DNA sequence in FIG. 1 or FIG. 2 or to fragments thereof; and (c) a DNA sequence which, but for the degeneracy of the genetic code, would hybridize to the DNA sequence in FIG. 1 or FIG. 2. Specifically comprehended in parts (b) and (c) are genomic DNA sequences encoding allelic variant forms of MI and/or encoding MI from other mammalian species, and manufactured DNA sequences encoding MI, fragments of MI, and analogs of MI which DNA sequences may incorporate codons facilitating transcription and translation of messenger RNA in microbial hosts. Such manufactured sequences may readily be constructed according to the methods of Alton et al., PCT published application WO 83/04053.

According to another aspect of the present invention, the DNA sequences described herein which encode MI polypeptides are valuable for the information which they provide concerning the amino acid sequence of the mammalian protein which have heretofore been unavailable. The DNA sequences are also valuable as products useful in effecting the large scale synthesis of MI by a variety of recombinant techniques. Put another way, DNA sequences provided by the invention are useful in generating new and useful viral and circular plasmid DNA vectors, new and useful transformed and transfected procaryotic and eucaryotic host cells (including bacterial and yeast cells and mammalian cells grown in culture), and new and useful methods for cultured growth of such host cells capable of expression of MI and its related products.

DNA sequences of the invention are also suitable materials for use as labeled probes in isolating human genomic DNA encoding MI and related proteins as well as cDNA and genomic DNA sequences of other mammalian species. DNA sequences may also be useful in various alternative methods of protein synthesis (e.g., in insect cells) or in genetic therapy in humans and other mammals. DNA sequences of the invention are expected to be useful in developing transgenic mammalian species which may serve as eucaryotic "hosts" for production of MI and MI products in quantity. See, generally, Palmiter et al., Science 222, 809-814 (1983).

The present invention provides purified and isolated polypeptide products having part or all of the primary structural conformation (i.e., continuous sequence of amino acid residues) and one or more of the biological properties (e.g., immunological properties and in vitro biological activity) and physical properties (e.g., molecular weight) of naturally-occurring MI including allelic variants thereof. The term "purified and isolated" as used herein means substantially homogeneous or purified to apparent homogeneity (e.g., one band by SDS-PAGE). These polypeptides are also characterized by being the natural purified product, or the product of chemical synthetic procedures or of procaryotic or eucaryotic host expression (e.g., by bacterial, yeast, higher plant, insect and mammalian cells in culture) of exogenous DNA sequences obtained by genomic or cDNA cloning or by gene synthesis. The products of expression in typical yeast (e.g., *Saccharomyces cerevisiae*) or procaryote (e.g., *E. coli*) host cells are free of association with any mammalian proteins. The products of expression in vertebrate (e.g., non-human mammalian (e.g. COS or CHO) and avian) cells are free of association with any human proteins. Depending upon the host employed, polypeptides of the invention may be glycosylated with mammalian or other eucaryotic carbohydrates or may be non-glycosylated. Polypeptides of the invention may also include an initial methionine amino acid residue (at position −1).

In addition to naturally-occurring allelic forms of MI, the present invention also embraces other MI products such as polypeptide analogs of MI and fragments of MI. Following the procedures of the above-noted published application by Alton et al. (WO 83/04053), one can readily design and manufacture genes coding for microbial expression of polypeptides having primary conformations which differ from that herein specified for in terms of the identity or location of one or more residues (e.g., substitutions, terminal and intermediate additions and deletions). Alternately, modifications of cDNA and genomic genes may be readily accomplished by well-known site-directed mutagenesis techniques and employed to generate analogs and derivatives of MI. Such products would share at least one of the biological properties of MI but may differ in others. As examples, projected products of the invention include those which are foreshortened by e.g., deletions; or those which are more stable to hydrolysis (and, therefore, may have more pronounced or longer lasting effects than naturally-occurring); or which have been altered to delete one or more potential sites for o-glycosylation (which may result in higher activities for yeast-produced products); or which have one or more cysteine residues deleted or replaced by, e.g., alanine or serine residues and are potentially more easily isolated in active form from microbial systems; or which have one or more tyrosine residues replaced by phenylalanine and bind more or less readily to target proteins or to receptors on target cells. Also comprehended are polypeptide fragments duplicating only a part of the continuous amino acid sequence or secondary conformations within MI, which fragments may possess one activity of MI (e.g., receptor binding) and not others (e.g., metalloproteinase inhibiting activity). It is noteworthy that activity is not necessary for any one or more of the products of the invention to have therapeutic utility [see, Weiland et al., Blut 44, 173-175 (1982)] or utility in other contexts, such as in assays of MI antagonism. Competitive antagonists may be quite useful in, for example, cases of overproduction of MI.

Of applicability to MI fragments and polypeptide analogs of the invention are reports of the immunological activity of synthetic peptides which substantially duplicate the amino acid sequence extant in naturally-occurring proteins, glycoproteins and nucleoproteins. More specifically, relatively low molecular weight polypeptides have been shown to participate in immune reactions which are similar in duration and extent to the immune reactions of physiologically significant proteins such as viral antigens, polypeptide hormones, and the like. Included among the immune reactions of such polypeptides is the provocation of the formation of specific antibodies in immunologically active animals. See, e.g., Lerner et al., Cell 23, 309-310 (1981); Ross et al., Nature 294, 654-656 (1981); Walter et al., Proc. Natl. Acad. Sci. USA 77, 5197-5200 (1980); Lerner et al., Proc. Natl. Acad. Sci. USA, 78 3403-3407 (1981); Walter et al., Proc. Natl. Acad. Sci. USA 78, 4882-4886 (1981); Wong et al., Proc. Natl. Acad. Sci. USA, 79 5322-5326 (1982); Baron et al., Cell 28, 395-404 (1982); Dressman et al., Nature 295, 185-160 (1982); and Lerner, Scientific American 248, 66-74 (1983). See, also, Kaiser et al. [Science 223, 249-255 (1984)] relating to biological and immunological activities of synthetic peptides which approximately share secondary structures of peptide hormones but may not share their primary structural conformation.

The present invention also includes that class of polypeptides coded for by portions of the DNA complementary to the protein-coding strand of the human cDNA or genomic DNA sequences of MI i.e., "complementary inverted proteins" as described by Tramontano et al. [Nucleic Acid Res. 12, 5049-5059 (1984)].

Also comprehended by the invention are pharmaceutical compositions comprising effective amounts of polypeptide products of the invention together with suitable diluents, preservatives, solubilizers, emulsifiers, adjuvants and/or carriers useful in MI therapy. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); covalent attachment of polymers such as polyethylene glycol to the protein; incorporation of the material into particulate preparations of polymeric compounds such as polylactic acid, polyglycolic acid, etc. or into liposomes. Such compositions will influence the physical state, stability, rate of in vivo release, and rate of in vivo clearance of MI.

The invention also comprises compositions including an additional metalloproteinase inhibitor such as TIMP or low molecular weight chemical inhibitors. It also comprises compositions including additional agents influencing progression of a disease state, e.g., laminin- and/or fibronectin-derived peptides which like MI can impede cancer metastasis.

Polypeptide products of the invention may be "labeled" by association with a detectable marker substance (e.g., radiolabeled with $^{125}$I) to provide reagents useful in detection and quantification of MI in solid tissue and fluid samples such as blood or urine. Nucleic acid products of the invention may also be labeled with detectable markers (such as radiolabels and non-isotopic labels such as biotin) and employed in hybridization processes to locate the human MI gene position and/or the position of any related gene family in a chromosomal map. They may also be used for identifying human MI gene disorders at the DNA level and used as gene markers for identifying neighboring genes and their disorders.

MI when used in pharmacological formulation modifies the pathogenesis and provides a beneficial therapy for diseases of connective tissues characterized by matrix degradation. Also, metalloproteinase inhibitor is useful in the treatment of any disorder where excessive matrix loss is caused by metalloproteinase activity, and in the promotion of wound healing following surgery.

Polypeptide products of the present invention are useful, alone or in combination with other drugs, in the treatment of various disorders such as dystrophic epidermolysis bullosa where the disease is linked to the overproduction of collagenase [Bauer et al., J. Exp. Med. 148, 1378-1387 (1978)]. The products of the present invention are also useful in the treatment of rheumatoid arthritis. Evanson et al. [J. Clin. Invest. 47, 2639-2651 (1968)] noted that large amounts of collagenase are produced, in culture, by excised rheumatoid synovial tissue; this led to immunolocalization studies, by Woolley et al. [Arthritis and Rheumatism 20, 1231-1239 (1977)] with monospecific antibodies directed against human rheumatoid synovial collagenase which detected high levels of immunoreactive collagenase at the sites of joint erosion (cartilage-pannus junctions) but not in the cartilage of associated chondrocytes, and not in the synovium at sites remote from the resorbing front. Collagenases have also been demonstrated using many other different preparations derived from human rheumatoid joints and using tissues characterized by other types of arthritis such as osteoarthritis, Reiter's syndrome, pseudogout, juvenile rheumatoid arthritis, and scleroderma.

In periodontal disease affecting the tooth supporting apparatus, elevation of collagenolytic enzymes is evident, and destruction of collagen and connective tissue [see V.-J. Uitto, pp. 211-223 in *Proteinases in Inflammation and Tumor Invasion*, H. Tschesche, ed., Walter de Gruyter & Co., Berlin, N.Y. (1988)].

Collagenases have been implicated in ulceration including corneal, epidermal, or gastric ulceration [Brown et al., American J. of Ophthalmology 72, 1139-1142 (1971)] and, indeed, metalloproteinase inhibitors are used in the treatment of corneal ulceration [Slansky et al., Annals of Ophthalmology 2, 488-491 (1970)].

In the field of tumor invasion and metastasis, the metastatic potential of some particular tumors correlates with the increased ability to synthesize and secrete collagenases [Liotta et al., Nature 284, 67-68 (1980)], and with the inability to synthesize and secrete significant amounts of a metalloproteinase inhibitor [Hicks et al., Int. J. Cancer 33, 835-844 (1984)]. These processes are related to the passage of tumor cells through connective tissue layers (basement membrane) from tissue sites to the circulation and vice-versa, which could be retarded by MI. MI similarly has therapeutic application in inhibiting tumor cell dissemination during removal of primary tumors or during chemotherapy and radiation therapy.

Tumors may also become more or less encapsulated or fibrotic due to increased collagen deposition (or inhibition of breakdown) by both cancer cells and/or surrounding normal cells. Increased encapsulation promoted by MI aids in clean tumor excision.

Other pathological conditions in which excessive collagen degradation may play a role and thus where MI can be applied, include emphysema, Paget's disease of bone, osteoporosis, scleroderma, pressure atrophy of bone or tissues as in bedsores, cholesteatoma, and abnormal wound healing.

MI also plays a role in the hematopoietic processes based on its erythroid potentiating activity (i.e., stimulation of differentiation of early erythroid progenitors), and thus MI is useful in the treatment of various anemias.

In addition MI has application in the treatment of immunological disorders such as autoimmune diseases (e.g., rheumatoid arthritis, multiple sclerosis) based upon its ability to suppress B-cell differentiation as determined by the method of Pisko et al. [J. Immunol. 136, 2141-2150 (1986)].

Based on its ability to inhibit proliferation of capillary endothelial cells, MI has application in cases where inhibition of angiogenesis is useful, e.g., in preventing or retarding tumor development.

The subject invention also relates to antibodies specifically binding metalloproteinase inhibitor. Example 6 below describes the production of polyclonal antibodies. A further embodiment of the invention is monoclonal antibodies specifically binding MI. In contrast to conventional antibody (polyclonal) preparations which typically include different antibodies directed against different determinants (epitopes), each monoclonal antibody is directed against a single determinant on the antigen. Monoclonal antibodies are useful to improve the selectivity and specificity of diagnostic and analytical assay methods using antigen-antibody binding. A second advantage of monoclonal antibodies is that they are synthesized by the hybridoma culture, uncontaminated by other immunoglobulins. Monoclonal antibodies may be prepared from supernatants of cultured hybridoma cells or from ascites induced by intra-peritoneal inoculation of hybridoma cells into mice. The hybridoma technique described originally by Köhler and Milstein [Eur. J. Immunol. 6, 511-519 (1976)] has been widely applied to produce hybrid cell lines that secrete high levels of monoclonal antibodies against many specific antigens.

The following examples are offered to more fully illustrate the invention, but are not to be construed as limiting the scope thereof.

Example 1

Purification/Characterization of Metalloproteinase Inhibitors from Bovine Aortic Endothelial Cell Conditioned Medium 1. Conditioned Medium.

Bovine aortic endothelial cells (cell line NCACl$_2$; DeClerck et al., Cancer Research, supra) were cultured in Eagle's Minimum Essential Medium (MEM) containing fetal bovine serum (2%, v/v) supplemented with MITO+ serum extender (2%, v/v; Collaborative Research, Inc., Bedford, Mass.), penicillin (100 U/ml) and streptomycin (100 µg/ml). Cells between passage 10 and 20 were grown in 800 cm$^2$ roller bottles (Costar). For conditioning, cultures at 80-90% confluence were washed 3 times with serum-free medium over 4 to 5 h and then incubated in the presence of fresh serum-free medium for 48 h. The medium was collected, centrifuged at 5,000×g for 10 min at 4° C. and kept at 4° C. after addition of sodium azide (0.02%, w/v). After the conditioning, cells were trypsinized, diluted 1:4 with medium, and grown to 80% confluence for reconditioning.

2. Inhibition Assays.

Purification work was monitored by inhibitory activity measured using a radiolabeled collagen film assay as described by Johnson-Wint [Anal. Biochem. 104, 175-181 (1980)]. The substrate used was $^{14}$C-acetylated rat skin collagen (about 300 cpm/µg) which was plated in a 96-well microtiter plate at 20 µl per well (about 6,000 cpm/well). The collagenase source was serum-free conditioned medium from 12-0-tetradecanoylphorbol-13-acetate (TPA)-treated rabbit synovial fibroblasts with a collagenase activity of approximately 8 units/ml (1 unit is the amount of enzyme that degrades 1 µg of collagen per min at 37° C.). Proenzyme was activated with trypsin (10 µg/ml) for 30 min at 22° C. and this was followed by inactivation of trypsin with a five-fold weight excess of soybean trypsin inhibitor. Various amounts of samples to be tested were incubated with the activated enzyme (40 mU) in a final volume of 200 µl also including Tris-HCl (50 mM) and Cad (10 mM) with pH of 7.5. These mixtures were then added to individual wells containing [$^{14}$C] collagen. After incubation at 37° C. for 3 h, supernatants were removed and counted in a beta scintillation counter. Percent inhibition was calculated by comparing the radioactivity released for cases containing samples tested with the radio activity released for the case containing collagenase alone. Background cpm values (buffer alone cases) were substracted from all cpm values. In the absence of inhibitor, 60 to 70% of the total radiolabeled substrate was degraded. One unit of inhibitor is defined as the amount that inhibits two units of collagenase by 50%, as determined from dose-inhibition curves.

For antigelatinase activity assays, $^{14}$C-labeled collagen was heat-denatured at 60° C. for 20 min and assay was performed in test tubes [Murphy et al., Biochem. J. 192, 517-525 (1980)]. Anti type IV collagenase activity was determined as described (DeClerck et al., Cancer Res., supra; and DeClerck, Arch. Biochem. Biophys., supra) using [$^{14}$C]proline-labeled type IV collagen extracted from the mouse Englebreth-Holm-Swarm tumor.

3. Purification.

All purification work was done at 4° C. unless otherwise indicated.

a. Concentrating.

Twenty liters of medium was concentrated using a Millipore Pellicon tangential flow ultrafiltration apparatus with a 10,000 molecular weight cutoff polysulfone membrane cassette (5 ft$^2$ total membrane area), to a volume of 450 ml. The sample was then further concentrated, to 64 ml, using an Amicon TCF 10 tangential flow ultrafiltration unit with an Amicon YM10 membrane. The non-ionic detergent Brij-35 was then added from a 10% (w/v) stock, to give a final concentration of 0.05% (w/v), and the sample was dialyzed against TNC/Brij-35 buffer [50 mM Tris-HCl, 200 mM NaCl, 0.05% (w/v) Brij-35, 10 mM CaCl$_2$, pH 7.5].

b. Gel Filtration.

The dialyzed sample (60 ml) was divided into three 20 ml portions, each of which was applied to a Sephadex G-100 gel filtration column (5×91 cm) equilibrated with TNC/Brij-35 buffer at 4° C. Flow rate was 60 ml/h and fractions of 13 ml were collected. For each column run, a chromatographic profile (absorbance at 280 nm and metalloproteinase inhibitor activity) essentially like that described in DeClerck et al., Cancer Research, supra, was obtained, with two peaks of inhibitor activity corresponding to apparent molecular weights of 70,000-75,000 and 30,000-35,000. The active fractions from each of the gel filtration column runs were pooled to yield peak I material (higher molecular weight) and peak II material (lower molecular weight).

c. Peak I Purification.

1. Anion Exchange.

The peak I material from gel filtration (312 ml; 3b above) was dialyzed against 20 mM Tris-HCl, 1 mM CaCl$_2$, 0.05% (w/v) Brij-35, pH 7.5 and applied in two separate chromatographic runs to a Mono Q anion exchange column (Pharmacia; 1 ml) equilibrated in the same buffer. A gradient from 0 to 0.5 M NaCl in the same buffer (total gradient volume of 60 ml) was then applied for elution of bound material. Chromatography was done at room temperature. Flow rate was 1 ml/min and fraction size 1 ml. FIG. 3 represents the elution profiles obtained. Activity represents collagenase inhibition measured as described in section 2 above, using aliquots (15 μl) from the indicated fractions. Fractions collected during sample application are not shown; no inhibitor activity was present in these fractions.

2. Chromatofocusing.

Figure 4:
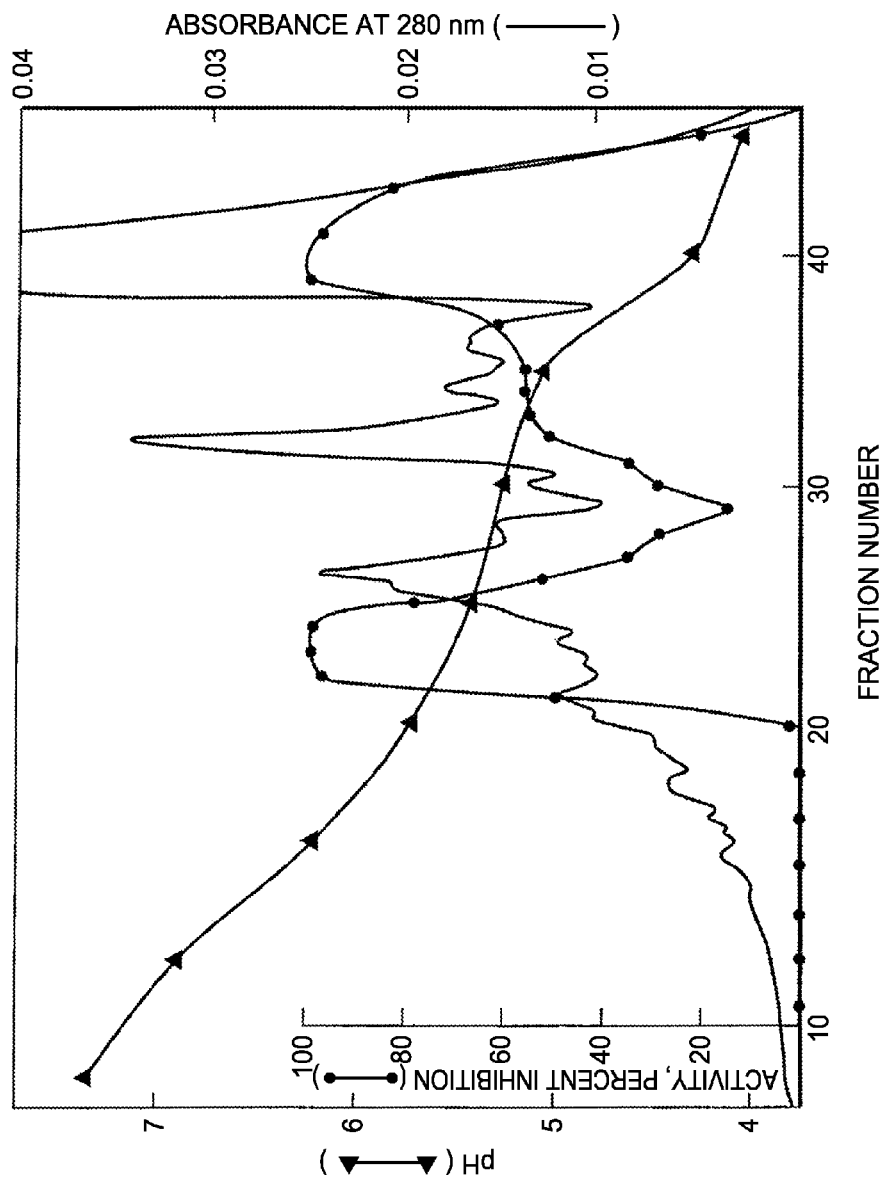
FIG. 4 shows chromatofocusing used in purification of bovine peak I-derived metalloproteinase inhibitor (MI).

The fractions from the Mono Q column runs that contained inhibitor activity were combined and the pool (12 ml) was dialyzed against 25 mM bis Tris-HCl, 1 mM CaCl$_2$, 0.05% (w/v) Brij-35, pH 7.4 and applied to a Mono P chromatofocusing column (Pharmacia; 4 ml) equilibrated in the same buffer, at room temperature. No inhibitor activity was present in fractions collected during sample application. Elution of bound material was accomplished with a pH gradient generated by applying a solution of polybuffer 74 (Pharmacia) diluted ten-fold and adjusted to pH 4 with HCl. Fractions of 1 ml were collected at a flow rate of 0.5 ml/min, immediately brought to 50 mM in Tris-HCl by addition of 50 μl of 1 M Tris-HCl, pH 7.5, and further titrated to pH 7.5 by addition of 2 M Tris base. The elution profile is shown in FIG. 4. Aliquots (5 μl) from the indicated fractions were measured for inhibitor activity as described in section 2 above. There is a peak of inhibitor activity eluting at about pH 5.5 (fractions 21-27), plus activity eluting later (fractions 30-45). These latter fractions were pooled, dialyzed against the Mono P starting buffer, and rechromatographed on the Mono P column as for the original sample. Recovered activity was redistributed between an earlier-eluting peak (about pH 5.5) and later-eluting region, with the early peak representing about one-third of the recovered activity. The later-eluting material from this second Mono P run was chromatographed again, with similar redistribution of the activity. The early-eluting fractions (pH 5.5 peak) from all three Mono P column runs were combined.

3. Gel Filtration.

The combined pool from the Mono P column runs (15 ml) was concentrated to 3 ml using Amicon Centricon 10 units centrifuged at 5000×g in a fixed-angle rotor. The concentrated sample was then applied to a Sephadex G-100 gel filtration column (1.5×94 cm) equilibrated with 50 mM Tris-HCl, 200 mM NaCl, 10 mM CaCl$_2$, pH 7.5. Fractions of 2.1 ml were collected, at a flow rate of 5 ml/h. A single peak of inhibitor activity was recovered, eluting with an apparent molecular weight of 24,000 relative to molecular weight markers used for column calibration (myoglobin, $M_r$ of 17,000; ovalbumin, $M_r$ of 44,000; gamma-globulin, $M_r$ of 158,000), and having a specific activity of about 1,550 U/mg.

In the purification of peak I-derived inhibitor, it should be noted that the second Sephadex G-100 gel filtration step was useful because the material at this stage behaved with an apparent molecular weight of 24,000 rather than the 70,000-75,000 true for peak I activity on the initial Sephadex G-100 column.

A summary of the purification for peak I-derived material is shown in Table 1.

Table I. (See following page.) Purification of two metalloproteinase inhibitors from bovine aortic endothelial cells. After steps 1 and 2, the inhibitors were separately purified as indicated. Recovery and degree of purification were calculated separately for the two inhibitor preparations, assigning values of 100% and 1, respectively, for each of the step 2 Sephadex G-100 peaks.

Footnotes:

[a]Determined by the method of Bradford [Anal. Bioch. 72, 248-254 (1976)] BSA as standard, except where indicated otherwise.

[b]Estimate, based on intensity of silver-stained bands after SDS-PAGE.

TABLE 1

| Step | Volume (ml) | Total protein (mg)[a] | Total activity (units) | Specific activity (units/mg) | Recovery (percent) | Purification (fold) |
|---|---|---|---|---|---|---|
| 1. Conditioned medium concentrated by ultrafiltration | 64 | 127 | 907 | 7.2 | — | — |
| 2. Sephadex G-100 | | | | | | |
| *Peak I-derived Inhibitor* | | | | | | |
| 2.1 Peak I | 312 | 22.5 | 202 | 9 | (100) | (1) |
| 2.1.1 Mono Q | 17 | 2.2 | 121 | 55 | 59 | 6 |
| 2.1.2 Mono P | 3 | ~0.1[b] | 62 | ~620 | 30 | 86 |
| 2.1.3 Sephadex G-100 | 12 | ~0.02[b] | 31 | ~1,550 | 15 | 172 |
| *Peak II-derived Inhibitor* | | | | | | |
| 2.2 Peak II | 470 | 16.4 | 695 | 42 | (100) | (1) |
| 2.2.1 Heparin-Sepharose | 7.5 | 2.6 | 330 | 126 | 47 | 3 |
| 2.2.2 Mono Q | 12 | 0.16 | 292 | 1,780 | 42 | 42 | d. Peak II Purification.
1. Heparin-Sepharose.

The peak II material from gel filtration (465 ml; 3b above) was dialyzed against 25 mM sodium cacodylate-HCl, 10 mM $CaCl_2$, 0.05% (w/v) Brij-35, pH 7.5 and chromatographed on a heparin-Sepharose column equilibrated with this buffer. After column washing, elution of bound material was achieved with a linear gradient to 1 M NaCl in the same buffer [see DeClerck, Arch. Biochem. Biophys. 265, 28-37 (1988)].

2. Anion Exchange.

The active fractions from heparin-Sepharose were combined (total volume 7.5 ml) and dialyzed against 20 mM Tris-HCl, 1 mM $CaCl_2$, pH 7.5. The material was then divided and applied in two separate chromatographic runs to a Mono Q column as described above (c.1). Eighty to 90% of the recovered activity was present in fractions collected during sample application (unbound), and represented highly-purified peak II-derived inhibitor material with a specific activity of about 1,780 U/mg. The remainder of the activity eluted early (about 0.065 M NaCl) in the salt gradient.

A summary of the purification for peak II-derived material is shown in Table 1.

4. Characterization of Peak I-Derived and Peak II-Derived Inhibitors.

a. SDS-PAGE was carried out by the method of Laemmli [Nature 227, 680-685 (1970)]. Stacking gels contained 4% (w/v) acrylamide and separating gels contained 12.5% (w/v) acrylamide. Samples were prepared under reducing or non-reducing conditions, that is, with or without 2-mercaptoethanol present in the treatment buffer. After electrophoresis, gels were subjected to silver-staining [Morrissey, Anal. Biochem. 117, 307-310 (1981)] or immunoblotting [Burnette, Anal. Biochem. 112, 195-203 (1981)].

1. Peak I-Derived Inhibitor.

The active fractions from the Sephadex G-100 column (c.3 above) all contained a fairly sharp major band evident upon SDS-PAGE with silver-staining, migrating with apparent molecular weight of 24,000-28,000 (reduced) and 19,000-22,000 (unreduced). This band was also evident in active fractions from the step that preceded (c.2 above; Mono P). Such co-elution of activity and material banding at this position is consistent with the conclusion that the band represents active protein. This band can be seen in FIG. 5A, lanes 1 and 2. For these gels, 100 µl of the final gel filtration pool (c.3 above; Table 1, step 2.1.3) was loaded; lane 1, reduced and lane 2, unreduced. Note that the difference in migration for the reduced and unreduced material probably reflects the presence of intrachain disulfide bonds in the unreduced case.

Figure 5:
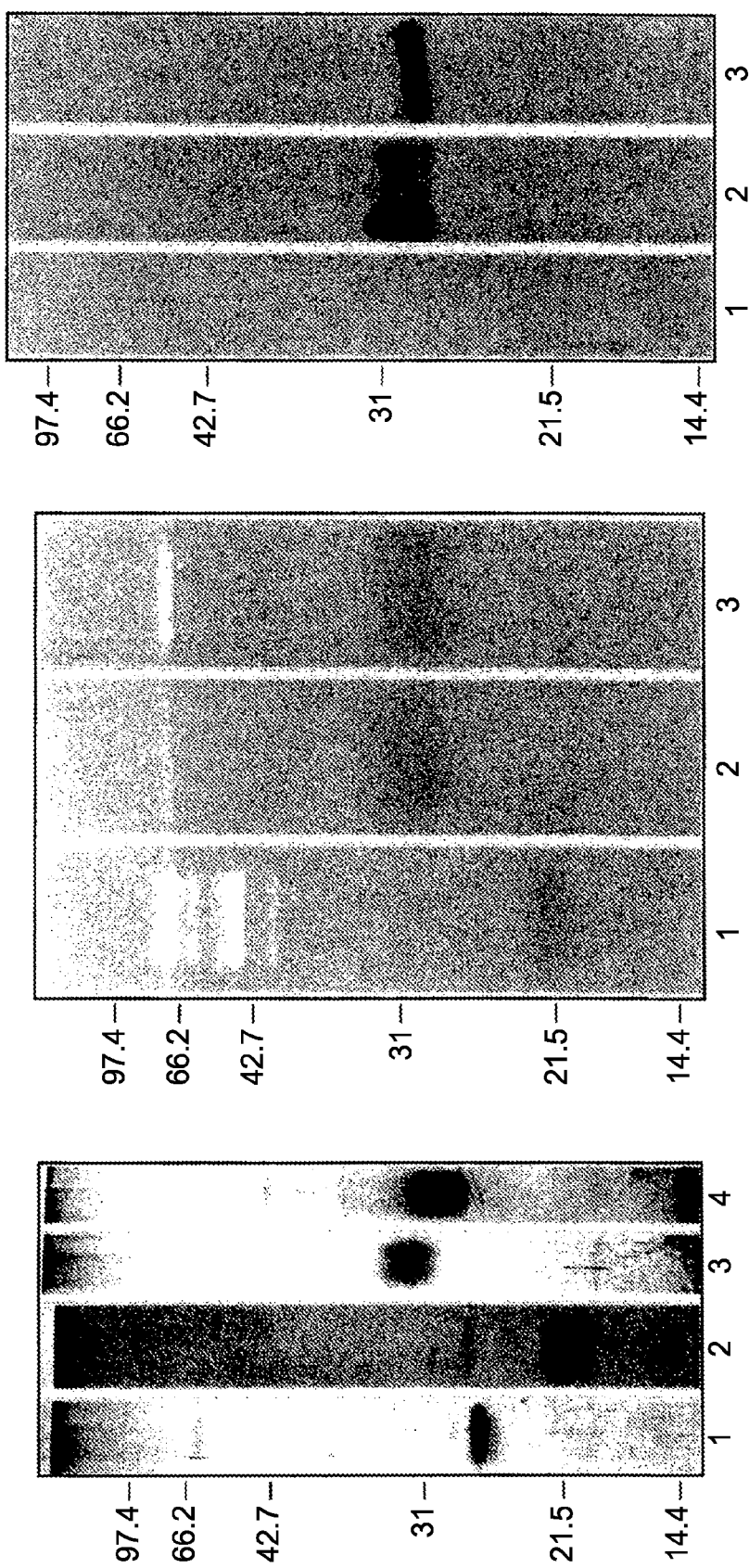
FIG. 5 shows sodium dodecyl sulfate (SDS)-polyacrylamide gel electrophoresis (PAGE) of bovine peak I-derived metalloproteinase inhibitor (MI) and peak II-derived metalloproteinase inhibitor. A is SDS-PAGE with silver-staining, B is SDS-gelatin PAGE, and C is SDS-PAGE with immunoblotting.

FIG. 5C, lane 1 shows the result of SDS-PAGE with immunoblotting for a similar sample (250 mU; unreduced). The primary antibody in the immunoblotting was a rabbit polyclonal antibody against TIMP from bovine vascular smooth muscle cells (DeClerck, Arch. Biochem. Biophys., supra) used at 1:500 dilution. (The secondary antibody used for detection was a goat anti-rabbit antibody conjugated with horseradish peroxidase.) No bands were visualized with the use of this primary antibody. Note that FIG. 5C, lane 3 shows that TIMP from bovine vascular smooth muscle cells (160 mU; unreduced) is visualized with the use of this antibody.

2. Peak II-Derived Inhibitor.

SDS-PAGE with silver-staining is shown in FIG. 5A, lanes 3 (reduced) and 4 (unreduced) for the unbound material from Mono Q chromatography (d.2 above; Table 1, step 2.2.2; 75 µl loaded). The staining material migrates over a fairly broad region representing a molecular weight range of 30,000-34,000 (reduced) and 27,000-31,000 (unreduced).

FIG. 5C, lane 2 shows that the peak II-derived inhibitor (240 mU loaded; unreduced) is visualized by SDS-PAGE with immunoblotting using the antibody against bovine vascular smooth muscle cell TIMP.

b. SDS-Gelatin PAGE.

The major bands on SDS-PAGE, as visualized by silver-staining, are also visualized, at the same molecular weight positions, with SDS-gelatin polyacrylamide gels, which identify proteins with inhibitory activity toward gelatinolytic enzymes [see Herron et al., J. Biol. Chem. 261, 2814-2818 (1986); DeClerck et al., Cancer Research, supra; and DeClerck, Arch. Biochem. Biophys., supra]. In this method, samples are subjected to SDS-PAGE, using gels with 10% (w/v) acrylamide and 0.1% (w/v) gelatin. The gels are then incubated in 2.5% (w/v) Triton X-100 for 1 h with two changes, to remove SDS, incubated for 3 h at 37° C. in 10 ml of p-aminophenylmercuric acetate (APMA)-activated conditioned medium from rabbit synovial fibroblasts to degrade gelatin, and then incubated overnight in 50 mM Tris-HCl, 10 mM $CaCl_2$, pH 7.5. The gels are then stained with Coomassie blue and destained with methanol:acetic acid:water (50:10:40). Bands having collagenase/gelatinase inhibitory activity show up as dark (blue) zones representing undegraded gelatin. The results of applying this method are shown in FIG. 5B for the following samples (all unreduced): lane 1, partially-purified peak I-derived inhibitor (50 mU loaded); lane 2, peak II-derived inhibitor (240 mU loaded); lane 3, bovine vascular smooth muscle cell TIMP (160 mU loaded). As mentioned, dark zones represent proteins with inhibitory activity toward gelatinolytic enzymes. The results further support the conclusion that the major silver-stained bands in the purified preparations represent the proteins with metalloproteinase inhibitor activity.

c. SDS-Gelatin PAGE with Proteinase Samples.

Figure 6:
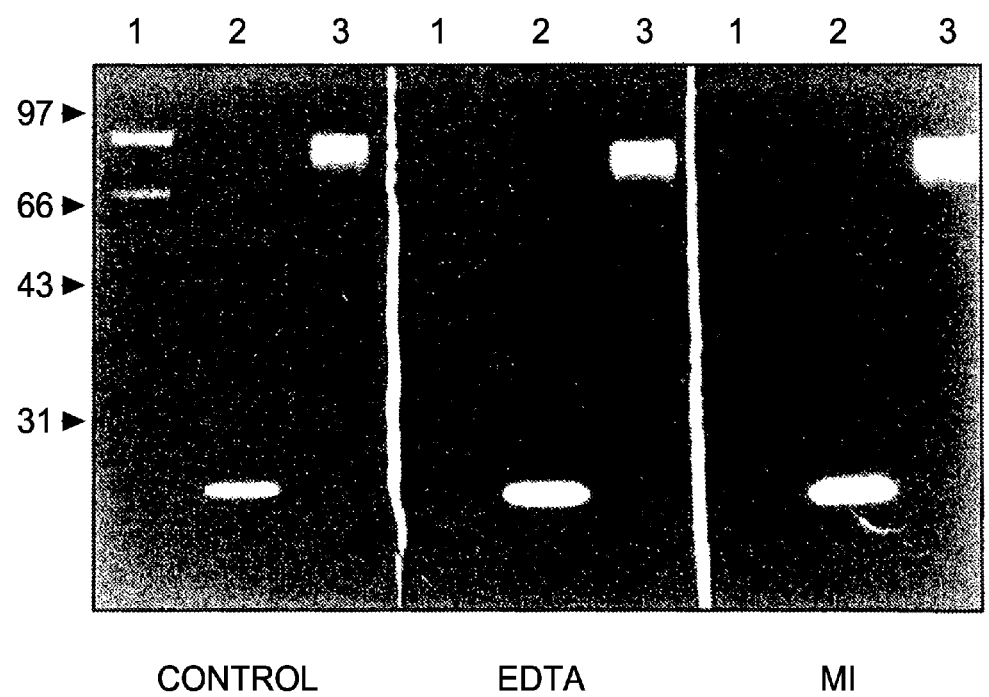
FIG. 6 shows effect of EDTA and of bovine peak I-derived metalloproteinase inhibitor (MI) on gelatinolytic proteinases run on SDS-gelatin PAGE.

To further test the preparations for inhibitory activity toward gelatinases, trypsin, or plasmin, samples containing the proteinases were electrophoresed on SDS-gelatin gels (supra). The gels were then incubated in 2.5% (w/v) Triton X-100 for 1 h with two changes, to remove SDS, and then incubated overnight in 50 mM Tris-HCl, 10 mM $CaCl_2$, pH 7.5 with or without the preparation being tested for inhibitory activity, stained with Coomassie blue, and destained (as in SDS-gelatin PAGE methods referred to, supra). See FIG. 6. For the lanes 1, 2 and 3 in this figure, electrophoresed samples were (respectively) APMA-activated conditioned medium from TPA-treated rabbit synovial fibroblasts (1.2 mU of collagenase activity; see section 2 of this Example), bovine trypsin (0.01 μg), and human plasmin (0.03 μg). In the case marked "MI", the overnight incubation of the gel included peak I-derived inhibitor (0.2 U/ml). Clear zones are indicative of gelatinolytic activity of the electrophoresed proteinase samples. Note by comparison to the "control" cases that "MI" inhibits the collagenases (clear zones at $M_r$ about 68,000 and 92,000 in "control" lane 1), but not trypsin or plasmin (which are not metalloproteinases). Similarly, it can be seen in FIG. 6 that the chelator "EDTA" (included at 20 mM) inhibited collagenases but not trypsin or plasmin, as expected.

d. Inhibition of Various Collagenases and Metalloproteinases.

Table 2 shows that peak I-derived material inhibited type I collagenase, gelatinase(s), and type IV collagenase, but did not inhibit bacterial collagenase.

TABLE 2

Effect of peak I-derived inhibitor on various collagenases

| Enzyme | Substrate | Peak I-derived inhibitor amount (mU) | Inhibition (%) |
|---|---|---|---|
| Type I collagenase[a] | $^{14}$C-labeled type I collagen[d] | 50 | 100 |
| Gelatinase[a] | $^{14}$C-labeled type I collagen, heat denatured[e] | 50 | 90 |
| Bacterial collagenase[b] | $^{14}$C-labeled type I collagen[d] | 200 | 0 |
| Type IV collagenase[c] | $^{14}$C-labeled type IV collagen[d] | 200 | 66 |

Figure 7:
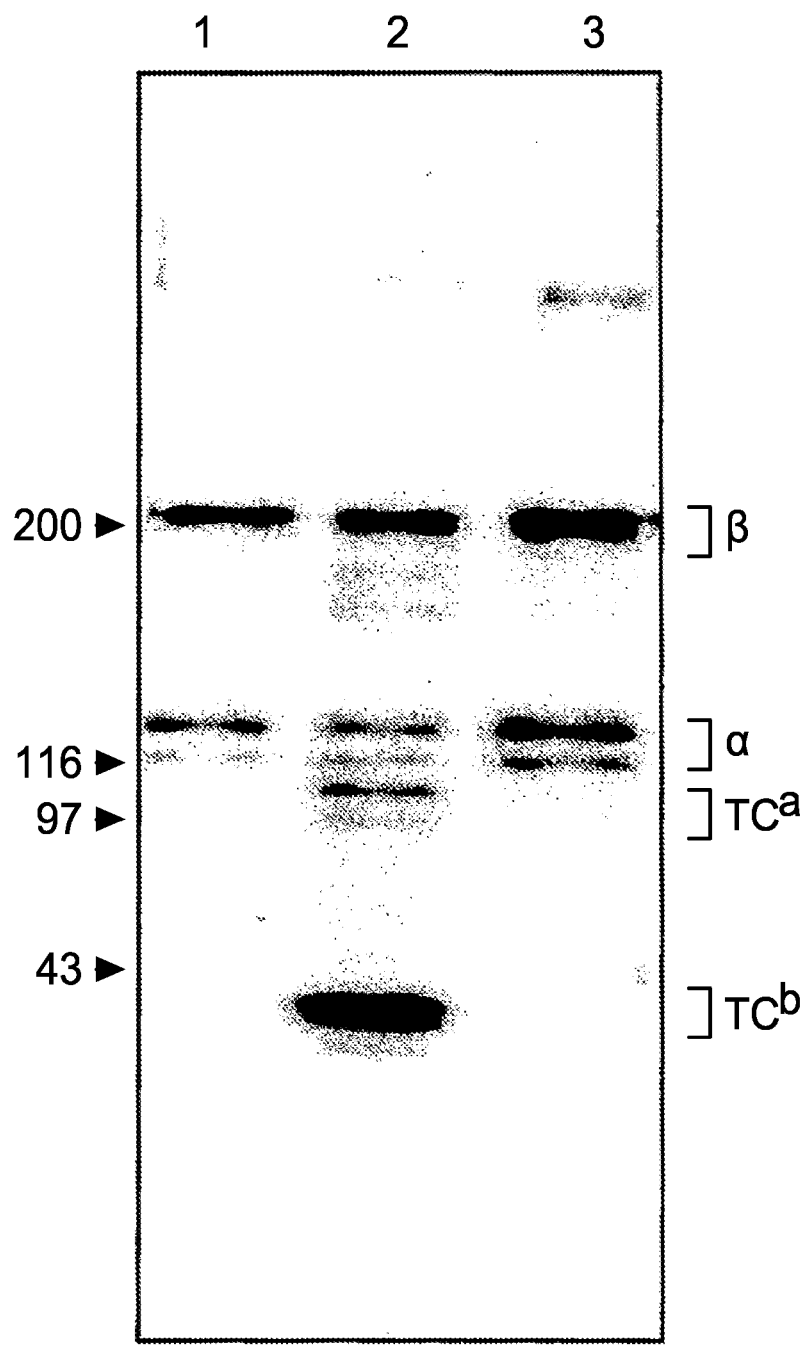
FIG. 7 shows autoradiography illustrating effect of bovine peak I-derived metalloproteinase inhibitor (MI) on specific collagen cleavage.

[a]Trypsin-activated conditioned medium from TPA-treated rabbit synovial fibroblasts (40 mU; see Example 1, section 2).
[b]Form III from Clostridium histolyticum (34 mU) (Advance Biofacture Corp., Lynbrook, NJ).
[c]Trypsin-activated conditioned medium from mouse reticulum cell sarcoma cell line (50 μl of 104-fold concentrated medium; see DeClerck, Arch. Biochem. Biophys., supra).
[d]See Example 1, section 2.
[e]Heat-denatured at 60° C. for 20 min.

e. SDS-PAGE of $^{14}$C-labeled collagen degradation products generated by type I (classical) collagenase in the absence and presence of the peak I-derived inhibitor is shown in FIG. 7. $^{14}$C-Labeled type I collagen (30,000 cpm) was incubated under the conditions described for inhibition assays in Example 1, section 2, with various additions, at 22° C. for 16 h. EDTA (20 mM) was then added to block metalloproteinase reactions, and samples were subjected to SDS-PAGE using a gradient gel (5-15% acrylamide). The gel was incubated in Autofluor (National Diagnostics, Manville, N.J.), dried and subjected to autoradiography. For FIG. 7: lane 1, no additions; lane 2, APMA-activated conditioned medium from TPA-treated rabbit synovial fibroblasts (5 μl of medium containing 40 mU of collagenase activity prepared as described in Example 1, section 2); lane 3, as lane 2, plus partially-purified peak I-derived inhibitor (50 mU). In the Figure, $TC^a$ and $TC^b$ represent the ¾-length and ¼-length fragments derived from single specific cleavage of the full-length α collagen polypeptide chains [Gross et al., Biochemistry 54, 1197-1204 (1965)], and B represents dimeric α chains. The results indicate that the inhibitory activity of peak I-derived inhibitor can be directed against the single peptide bond cleavage located one quarter of the distance from the COOH-terminus and characteristic of mammalian collagenase.

f. The purified peak I-derived and peak II-derived materials have been characterized with regard to susceptibilities to heat, acid, reduction-alkylation, and trypsin treatment. The results are shown in Table 3.

TABLE 3

Stability of peak I-derived and peak II-derived inhibitors. Inhibitor samples (2 U/ml) were treated as indicated prior to being tested for residual anticollagenase activity determined from dose-inhibition curves.

| | | | Loss of inhibitory activity (%) | |
|---|---|---|---|---|
| Treatment | | Conditions | Peak I-derived inhibitor | Peak II-derived inhibitor |
| (A) | Heat[a] | 37° C. | 0 | 11 |
| | | 50° C. | 0 | 11 |
| | | 80° C. | 9 | 30 |
| | | 100° C. | 59 | 44 |
| (B) | Trypsin[b] | 1:1 | 10 | 0 |
| | | 10:1 | 28 | 21 |
| | | 50:1 | 100 | 100 |
| (C) | Acid | pH 4.5, 22° C., 1 h | 0 | 0 |
| (D) | Reduction-alkylation[c] | | 100 | 100 |

[a]Inhibitor samples were incubated at indicated temperatures for 1 h. Loss of inhibitory activity was calculated in comparison with an untreated sample.
[b]Samples were incubated at indicated trypsin:inhibitor ratios (w:w) for 1 h at 37° C. The reaction was then blocked with five-fold weight excess of soybean trypsin inhibitor. Loss of activity was determined in comparison with a sample incubated at 37° C. for 1 h in the presence of a trypsin-soybean trypsin inhibitor mixture.
[c]Samples were reduced by the addition of 2-mercaptoethanol (20 mM) for 16 h at 4° C. and alkylated with iodoacetamide (20 mM) at 30° C. for 1 h. Loss of activity was determined by comparison with samples incubated at the same temperatures. 2-Mercaptoethanol and iodoacetamide did not affect collagenase activity.

Example 2

Amino-Terminal Amino Acid Sequence Analysis of Peak I-Derived Inhibitor and Peak II-Derived Inhibitor; Amino Acid Composition Analysis of Peak I-Derived Inhibitor Peak I-derived inhibitor (4.8 ml; Table 1, step 2.1.3) was concentrated and introduced into 50 mM ammonium bicarbonate, pH 7.8 using an Amicon Centricon 10 ultrafiltration unit. The sample was spotted onto a glass fiber disc on a sequencer cartridge, which had been pre-cycled with polybrene. The glass fiber disc containing sample was dried under a stream of $N_2$. Amino-terminal amino acid sequence analysis was performed according to published methods [Hewick et al., J. Biol. Chem. 256, 7990-7997 (1981)] with Applied Biosystems Model 477 protein sequencer using a standard program provided by Applied Biosystems (Foster City, Calif.). The released phenylthiohydantoin (PTH)-amino acids were analyzed by a Model 120 on-line PTH-amino acid analyzer using a Brownlee reverse phase C-18 column. The chromatograms obtained were analyzed by a Model 900 data module. An initial yield of approximately 158 pmol was obtained with an average repetitive yield of 94%. Amino acid assignments at 42 positions were made. In a repeat sequencing run, the assignments were completely identical to those of the first sequencing run except that three more amino acids (positions 43-45) were assigned. Table 4 shows the assigned amino-terminal amino acid sequence.

TABLE 4

Amino-terminal sequence of bovine peak I-derived inhibitor

```
  1     2     3     4     5     6     7     8     9    10    11
(Cys)-Ser-(Cys)-Ser-Pro-Val-His-Pro-Gln-Gln-Ala- 12    13    14    15    16    17    18    19    20    21    22
Phe-(Cys)-Asn-Ala-Asp-Ile-Val-Ile-Arg-Ala-Lys- 23    24    25    26    27    28    29    30    31    32    33    34
Ala-Val-Asn-Lys-Lys-Glu-Val-Asp-Ser-Gly-Asn-Asp- 35    36    37    38    39    40    41    42    43    44    45
Ile-Tyr-Gly-Asn-Pro-Ile-Lys-Arg-Ile-Gln-Tyr-----
```

Residues 1, 3 and 13 were assigned as cysteines since no other assignments could be made for these cycles and cysteine is undetectable by the sequencing methods used.

In order to compare sequence, a preparation of purified peak II-derived inhibitor (2.25 ml; Table 1, step 2.2.2; prepared as described for peak I-derived inhibitor) was also subjected to amino-terminal sequence analysis. The sequence shown in Table 5 was obtained.

TABLE 5

Amino-terminal sequence of bovine peak II-derived inhibitor

```
  1     2     3     4     5     6     7     8     9    10    11
(Cys)-Thr-(Cys)-Val-Pro-Pro-His-Pro-Gln-Thr-Ala- 12    13    14    15    16    17    18    19    20    21    22
Phe-(Cys)-Asn-Ser-Asp-Val-Val-Ile-Arg-Ala-Lys- 23    24    25    26    27    28    29    30    31    32    33
Phe-Val-Gly-Thr-Ala-Glu-Val-(Asn)-Glu-Thr-Ala- 34    35    36    37    38    39    40    41    42    43    44
Leu-Leu-Tyr-Arg-Tyr-Leu-Ile-Lys-Met-[Leu]-Lys- 45    46    47    48    49
Met-Pro-Ser-[Gly]-Phe---
```

The initial yield was approximately 280 pmol and the average repetitive yield was 92%. Residues 1, 3 and 13 were assigned as cysteines for the reasons described above. Residue 30 was also not recovered and was assigned as asparagine since the subsequent sequence (Asn-Gly-Thr . . . )
  30 31 32
would be consistent with an Asn-linked glycosylation site. The assignments at positions 43 and 48 (in brackets) were made with less than full confidence.

Based on these various analyses (Examples 1 and 2), the peak II-derived material is almost certainly bovine TIMP. Human TIMP is very well characterized and has been cloned (Docherty et al., Nature, supra; Carmichael et al., Proc. Natl. Acad. Sci. USA, supra). Comparing the amino-terminal sequences of human TIMP and the peak II-derived material, the homology over the first 29 residues is 93% and the homology over the first 49 residues is 80% (see Table 6). In addition the isolated bovine peak II-derived material shares many of the biochemical properties of TIMP, i.e., behavior in various purification steps, mobility on SDS-PAGE, and recognition by antibody to bovine smooth muscle TIMP in SDS-PAGE with immunoblotting (Example 1).

The peak I-derived material (MI) is clearly distinct from TIMP (Table 6) in amino acid sequence, but does have homology to TIMP. Homology over the first 29 residues is 65%, and homology over the first 45 residues is 47%. The molecules have different chromatographic behaviors, different mobilities on SDS-PAGE, and antibody to bovine smooth muscle TIMP does not visualize the peak I-derived material in immunoblots after SDS-PAGE (Example 1). This novel peak I-derived inhibitor is designated metalloproteinase inhibitor (MI).

Over the first 45 residues, the peak I-derived and peak II-derived bovine inhibitors have 51% homology to each other.

TABLE 6

Comparison of the amino-terminal sequence of (1) human TIMP[a], (2) bovine peak II-derived inhibitor (TIMP)[b] and (3) bovine peak I-derived inhibitor (MI)[c]

```
                  1                   10                  20
1 HUMAN        C T C V P P H P Q T A F C N S D L V I R
  TIMP
2 BOVINE       C T C V P P H P Q T A F C N S D V V I R
  TIMP
3 BOVINE       C S C S P V H P Q Q A F C N A D I V I R
  MI
                 21                   30                  40
1 HUMAN        A K F V G T P E V N Q T T L Y Q R Y E I
  TIMP
2 BOVINE       A K F V G T A E V N E T A L L Y R Y L I
  TIMP
3 BOVINE       A K A V N K K E V D S G N D I Y G N P I
  MI
                 41                   49
1 HUMAN        K M   T   K M Y K   G   F
  TIMP
2 BOVINE       K M (L) K M P S (G) F . . .
  TIMP
3 BOVINE       K R   I   Q Y
  MI
```

[a]From Docherty et al., Nature, supra; and Carmichael et al., Proc. Natl. Acad. Sci. USA, supra.
[b,c]From sequence analyses described in Example 2.

The amino acid composition of the bovine peak I-derived inhibitor (MI) is shown in Table 7. A sample of peak I-derived inhibitor (1.2 ml; Table 1, step 2.1.3) was concentrated and introduced into 50 mM ammonium bicarbonate, pH 7.8 using an Amicon Centricon 10 ultrafiltration unit. The sample was then dried and subjected to amino acid composition analysis by the method described by Lu et al. [J. Chromatog. 368, 215-231 (1986)]. This involved chromatographic analysis of phenylthiocarbamyl-amino acids generated after acid hydrolysis (24 h) of the samples. Data from three separate chromatographic analyses were used to estimate average residues per molecule values. For each of these analyses an amount of material derived from one-tenth of the starting sample was used. The value for total amino acids (178) used in calculating residues per molecule was taken from the gene-encoded sequence for the mature bovine MI (Example 3, FIG. 1).

TABLE 7

Amino acid composition analysis of bovine peak I-derived inhibitor (MI)

| Amino acid | Residues per molecule | | |
|---|---|---|---|
| | Average value | Integral value | "Actual" value[c] |
| Lys | 15.5 | 16 | 17 |
| His | 3.6 | 4 | 4 |
| Arg + Thr[a] | 15.9 | 16 | 6 + 6 = 12 |
| Asx[1] | 22.9 | 23 | 22 |
| Ser | 10.9 | 11 | 10 |
| Glx[1] | 19.4 | 19 | 19 |
| Pro | 8.1 | 8 | 12 |
| Gly | 14.2 | 14 | 13 |
| Ala | 15 | 15 | 16 |
| Val | 9 | 9 | 8 |
| ½-Cys | nd[b] | | (12) |
| Met | 3.1 | 3 | 5 |
| Ile | 14.6 | 15 | 19 |
| Leu | 10.8 | 11 | 7 |
| Tyr | 7.1 | 7 | 7 |
| Phe | 7.7 | 8 | 7 |
| Trp | nd[b] | | (4) |
| | 178 | 179 | 78 + 12 + 4 = 194 |

[a]Arg and Thr were not separable by the method used.
[b]Not determined.
[c]Values from gene-encoded sequence of nature bovine MI polypeptide; see Example 3, FIG. 1.

Example 3

Cloning of the Bovine and Human Metalloproteinase Inhibitor Genes

The amino-terminal amino acid sequence for the bovine metalloproteinase inhibitor was determined as described above and 3 probes were designed and manufactured on DNA synthesizers (Applied Biosystems models 380A and 380B) for hybridization to the sense strand of DNA (or to the mRNA). The first probe was designed as a long nondegenerate probe by the method of Lathe [J. Mol. Biol. 183, 1-12 (1985)] to recognize the region corresponding to amino acids 4 to 19 and is as follows:
5' GAT CAC AAT GTC AGC ATT GCA GAA GGC CTG CTG GGG ATG CAC AGG 3'
The second and third probes were designed as degenerate probes incorporating inosine bases at positions of 4-fold degeneracy. The second probe recognizes the region corresponding to amino acids 21 to 30 and is as follows:

```
                (T)   (T)   (T)
5' GTC IAC (C)TC (C)TT (C)TT GTT IAC IGC (T)
   (C)TT IGC 3'
```

The parentheses indicate the incorporation of two bases, leading to multiple oligonucleotides in the probe preparation. The third probe recognizes the region corresponding to amino acids 32 to 41 and is as follows:

```
                    (A)      (A)      (A)
5' CTT IAT IGG (G)TT ICC (G)TA IAT (G)TC (A)
   (G)TT ICC 3'
```

A λgt11 cDNA library, made with mRNA isolated from bovine aorta endothelial cells, was purchased from CLONTECH Laboratories, Inc. (Palo Alto, Calif.). Approximately 10⁶ phage were plated onto eight 23×23 cm square plates with the host bacterial strain, Y1090. Two lifts from each plate were made onto GeneScreen Plus (Dupont) hybridization transfer membranes. One set of membranes was hybridized with $^{32}$P-phosphorylated probe 2 and the other set of membranes was hybridized with $^{32}$P-phosphorylated probe 3. Hybridizations were done overnight in 6×SSC, 5×Denhardts, 0.5% (w/v) SDS, 50 µg/ml sheared and denatured herring sperm DNA at 50-55° C. The filters were washed in 6×SSC, 0.5% (w/v) SDS at approximately 55° C. After autoradiography, three clones were identified which hybridized to both probes. These clones were rescreened until isolated plaques were obtained for each. Mini λ phage preps were made for each of the three clones using the LambdaSorb Phage Adsorbent from Promega. Restriction endonuclease digests of the three clones using several restriction enzymes indicated that all three clones were identical and were obtained due to amplification of the cDNA library by the supplier. By Southern blotting analysis, the same restriction fragments were found to hybridize not only to probes 2 and 3, but to probe 1 as well. The restriction endonuclease analysis indicated that the rightward EcoRI site had been abolished during the cDNA cloning. Therefore, the cDNA-containing fragment from the leftward EcoRI site to an SstI site in λgt11 approximately 1 kilobase (kb) from the abolished EcoRI site was cloned into pUC19 to generate pUC BMI. Overlapping restriction fragments of both orientations were subsequently cloned from pUC BMI into M13 mp vectors to obtain the sequence of the gene using the dideoxy method of Sanger et al. [Proc. Natl. Acad. Sci. USA 74, 5463-5467 (1977)]. As shown in FIG. 1, the gene codes for a mature protein of 194 amino acids with a leader sequence of 26 amino acids. The first 45 amino acids of the mature protein exactly match the amino-terminal sequence determined for the purified protein (Example 2). In addition, the amino acid composition as determined from the gene-encoded sequence of the mature bovine MI polypeptide is in agreement with that obtained experimentally for the bovine peak I-derived inhibitor (see Example 2, Table 7), providing further evidence that the cloned gene corresponds to the purified MI polypeptide of Example 1. The molecular weight of the mature bovine MI polypeptide chain, based on the gene-encoded sequence in FIG. 1, is 21,693.

Four long oligonucleotide probes (51-mers), which exactly match the sequences of the antisense strand of the bovine metalloproteinase inhibitor coding region, were manufactured on DNA synthesizers (Applied Biosystems models 380A and 380B) in order to screen human cDNA libraries for the human MI gene sequences. The 4 sequences were as follows:
probe 1
5' CGG GTC CTC GAT GTC CAG AAA CTC CTG CTT GGG GGG TGC TGC TCC GCG GTA 3'
probe 2
5' GAA CTT GGC CTG GTG TCC GTT GAT GTT CTT CTC CGT GAC CCA GTC CAT CCA 3'
probe 3
5' GCA CTC ACA GCC CAT CTG GTA CCT GTG GTT CAG GCT CTT CTT CTG GGT GGC 3'
probe 4
5' GGG GTT GCC GTA GAT GTC GTT GCC AGA GTC CAC CTC CTT CTT ATT GAC TGC 3'
A λgt11 cDNA library made with mRNA isolated from human heart tissue (fetal aorta) was purchased from CLONTECH Laboratories, Inc. Approximately 10⁶ phage were plated onto eight 23×23 cm square plates with the host bacterial strain, Y1090. Two lifts from each plate were made onto GeneScreen Plus hybridization transfer membranes. One set of membranes was hybridized with a mixture of $^{32}$P-phosphorylated probes 1 and 2, and the second set of membranes was hybridized with a mixture of $^{32}$P-phosphorylated probes 3 and 4, using the hybridization and wash conditions described above. Three clones hybridized to both sets of probes and these clones were rescreened until isolated plaques were obtained. Mini λ phage DNA preps were made as described above and restriction endonuclease digests were performed on the DNAs. The three clones were of similar but different lengths so one of the clones was subcloned from λgt11 into M13 mp9 from EcoRI to EcoRI in both orientations. This EcoRI fragment was subsequently cloned from M13 mp 9 into pUC19 to generate pUC HMI. The original clones in M13 mp 9 and additional overlapping restriction fragments cloned from pUC HMI into M13 mp vectors in both orientations were sequenced using the dideoxy method of Sanger (Proc. Natl. Acad. Sci. USA, supra). The sequence of the human metalloproteinase inhibitor gene is shown in FIG. 2. It, like the bovine metalloproteinase inhibitor gene, codes for a protein of 194 amino acids with a leader sequence of an additional 26 amino acids. The two genes code for different amino acids at 11 of the 194 residues corresponding to the mature protein. The molecular weight of the mature human MI polypeptide, based on the gene-encoded sequence in FIG. 2, is 21,730.

Example 4

Expression of Recombinant Human Metalloproteinase Inhibitor in *E. coli*

Figure 8:
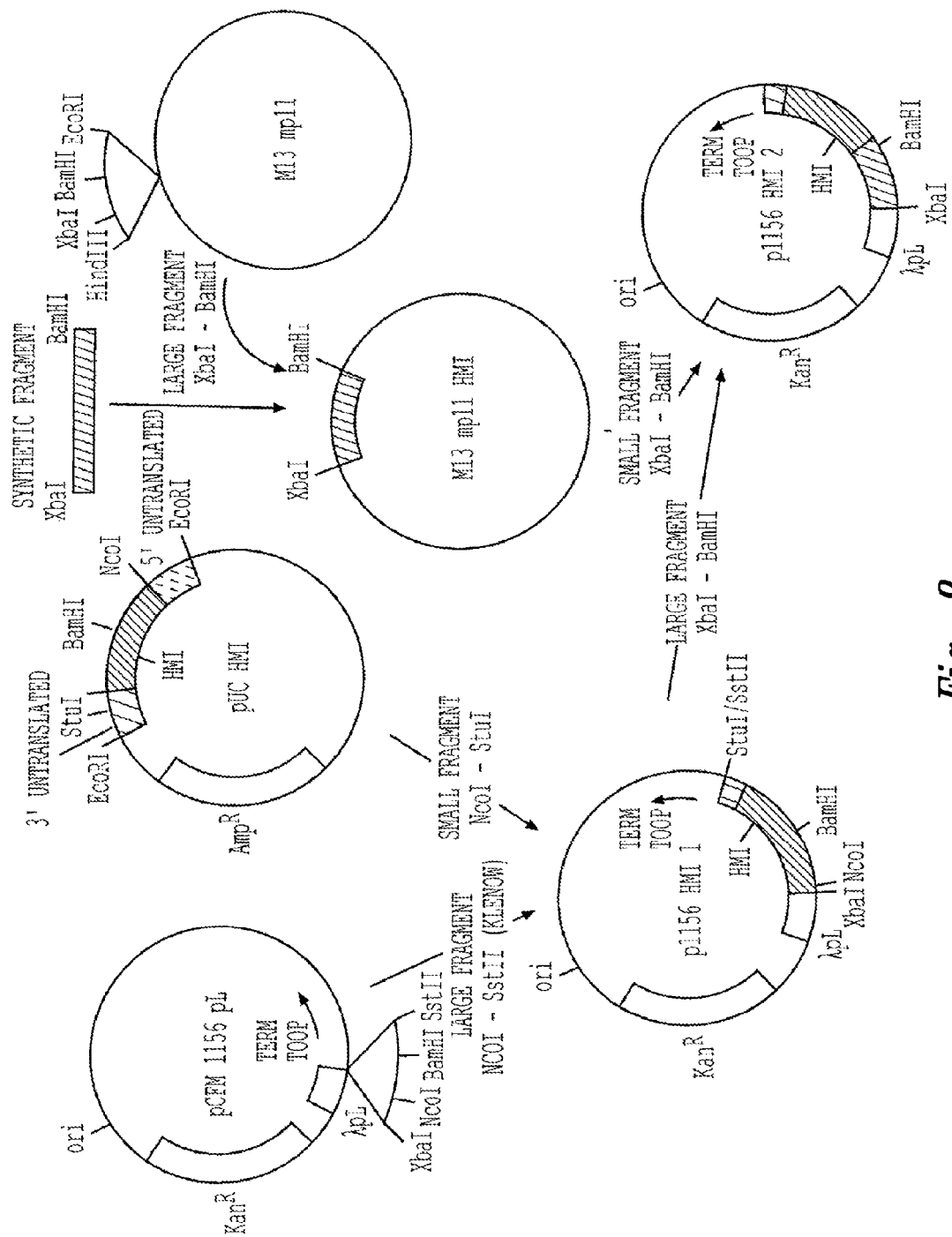
FIG. 8 shows a diagram of plasmid constructions made for expression of recombinant human metalloproteinase inhibitor in *Escherichia coli*.

The mature human metalloproteinase inhibitor protein was expressed in *E. coli* by utilizing an NcoI site at amino acid 1 of the leader sequence, a BamHI site at amino acid 42 of the mature protein, and a StuI site 3 nucleotides downstream from the termination codon. The fragment from NcoI to StuI was first cloned into an expression vector, pCFM 1156 µL, from NcoI to SstII (which had been blunted at the SstII site using the Klenow fragment of DNA polymerase I) to generate p1156 HMI1 (FIG. 8). The plasmid pCFM 1156 µL can be derived from plasmid pCFM 836 (see U.S. Pat. No. 4,710,473 hereby incorporated by reference), by destroying the two endogenous NdeI restriction sites by end filling with T4 polymerase enzyme followed by blunt end ligation, replacing the DNA sequence between the unique AatII and ClaI restriction sites containing the synthetic pL promoter with a similar fragment obtained from pCFM 636 (see U.S. Pat. No. 4,710, 473) containing the pL promoter, and substituting the small DNA sequence between the unique ClaI and KpnI restriction sites with the following oligonucleotide:

A synthetic DNA fragment was constructed which contained a ribosome binding site, an initiation methionine codon, and codons for the first 42 amino acids of the mature human MI (FIG. 9). This fragment was first cloned into M13 mp11 from XbaI to BamHI to confirm the sequence by the dideoxy method of Sanger (Proc. Natl. Acad. Sci. USA, supra). This XbaI to BamHI fragment was then cloned from M13 mp11 into p1156 HMI1 to generate p1156 HMI2 (FIG. 8).

This plasmid was transformed into *E. coli* strain FM5 (ATCC deposit no. 539111 deposited May 19, 1989) which contains a temperature-sensitive λCI repressor on the chromosome. The plasmid contains the λpL promoter/operator region and has a temperature sensitive replicon. When *E. coli* strain FM5 harboring p1156 HMI2 is cultured at 28° C., the plasmid copy number is maintained at 10-20 copies/cell, and transcription from the λpL promoter is regulated by a temperature-sensitive repressor. Growth at 42° C. results in an increased copy number and a release of repression at the λpL promoter. Recombinant human metalloproteinase inhibitor begins to accumulate at elevated temperatures as a result of promoter activation and plasmid amplification. The λpL promoter lies just upstream from the ribosome binding site and the methionine initiation codon of human metalloproteinase inhibitor. The transcription terminator, t-oop, lies just downstream from the two translational stop codons near the 3' end of the gene. Strain FM5 harboring the plasmid p1156 HMI2 was grown using the dual-feed media described by Tsai et al. [J. Indust. Microbiol. 2, 181-187 (1987)]. Induction was accomplished by a temperature shift to 42° C. when the optical density at 600 nm ($OD_{600}$) had reached about 30. The final $OD_{600}$ reached approximately 60. Recombinant human MI was expressed up to a level of 15 mg/OD-liter. The human MI was evident after SDS-PAGE with Coomassie blue staining (load equivalent to 0.4 mg wet weight of cells; reduced) as a prominent band with $M_r$ 24,000-28,000 which co-migrated with the band for purified bovine MI (Example 1). Other *E. coli* host cells can be used for expression as will be apparent to those skilled in the art.

Example 5

Purification of *E. coli*-Expressed Recombinant Human Metalloproteinase Inhibitor The human MI is expressed in *E. coli* in insoluble, inactive form (so-called inclusion bodies). Isolation of active MI requires procedures for solubilization, purification, folding, and oxidation (disulfide formation) of the inclusion body MI. An example of such procedures is given below.

```
       ClaI                                                     KpnI
5'     CGATTTGATTCTAGAAGGAGGAATAACATATGGTTAACGCGTTGGAATTCGGTAC    3'

3'         TAAACTAAGATCTTCCTCCTTATTGTATACCAATTGCGCAACCTTAAGC        5'
```

The pL promoter DNA sequence inserted is as follows:

```
       AatII
5'        CTAATTCCGCTCTCACCTACCAAACAATGCCCCCCTGCAAAAAATAAATTCATAT
3'     TGCAGATTAAGGCGAGAGTGGATGGTTTGTTACGGGGGGACGTTTTTTATTTAAGTATA

AAAAAACATACAGATAACCATCTGCGGTGATAAATTATCTCTGGCGGTGTTGACATAAA
       TTTTTTGTATGTCTATTGGTAGACGCCACTATTTAATAGAGACCGCCACAACTGTATTT

TACCACTGGCGGTGATACTGAGCACAT    3'
       ATGGTGACCGCCACTATGACTCGTGTAGC   5'
                                ClaI
```

About 400 grams (wet weight) of cell paste of *E. coli* strain FM5 harboring plasmid p1156 HMI2, grown as indicated in Example 4, was suspended in 1.5 liters of $H_2O$. The material was passed through a Manton-Gaulin homogenizer three times and then centrifuged for 45 min at about 4,000×g at 4° C. The supernatent was poured off and discarded. The pellets were resuspended in 1.5 liters $H_2O$ (4° C.) and centrifuged as above. The supernatant was poured off and discarded. The pellets were resuspended in 120 ml $H_2O$ and then diluted ten-fold with 20 mM Tris-HCl, pH 9.5. The pH was adjusted to 11.5 (using 1 N NaOH), and the mixture was left on ice for 15 min, and then centrifuged for 30 min at 11,300×g at 4° C. The supernatent was diluted four-fold with 20 mM Tris-HCl, pH 9.5. The pH was adjusted to 10-10.5 (with 1N NaOH) and the mixture was stirred overnight at room temperature.

The pH of the mixture was lowered to 8.5 (using 1N HCl) and the mixture was then loaded onto a DEAE-Sepharose Fast Flow (Pharmacia) ion exchange column (150 ml column volume) equilibrated in 20 mM Tris-HCl, pH 8.5. Bound material was eluted with a 2 liter gradient from 0 to 0.3 M NaCl in the Tris-HCl buffer. Fractions of 12 ml were collected at a flow rate of 8 ml/min. Aliquots (25 μl) of collected fractions were subjected to SDS-PAGE (15%, w/v, acrylamide; unreduced) with Coomassie blue staining. Fractions 38-54, which contained a fairly sharp band ($M_r$ about 22,000-23,000) corresponding to the MI polypeptide, were pooled (202 ml). Material thought to also represent the MI polypeptide, but having a slightly lower mobility and banding less sharply on SDS-PAGE, eluted later in the gradient and was not included in the pool.

The pooled material from DEAE-Sepharose Fast Flow was concentrated to 30 ml using an Amicon stirred cell (with YM5 membrane). The pH was adjusted to 5.4 (using 50% acetic acid) and the mixture was dialysed against 20 mM sodium acetate, pH 5.4. The material was then diluted with $H_2O$ to a final volume of 45 ml and applied to a CM-Sepharose Fast Flow (Pharmacia) ion exchange column (1 ml column volume) equilibrated in 20 mM sodium acetate, pH 5.4. Bound material was eluted using a 20 ml gradient from 0 to 0.4 M NaCl in the sodium acetate buffer. Fractions of 1 ml were collected at a flow rate of 0.1 ml/min. Aliquots (10 μl) of the fractions were analyzed by SDS-PAGE as above and those containing MI [fractions 11-18 (8 ml)] were pooled and then loaded directly onto a Sephacryl S-200 HR gel filtration column (300 ml column volume) equilibrated in phosphate-buffered saline (PBS). Fractions of 4 ml were collected at a flow rate of 20 ml/h. Aliquots (20 μl) of the fractions were again analyzed by SDS-PAGE as above. Fractions 54-60 contained MI; to maximize purity, only fractions 56-59 were pooled (16 ml). Purity of MI in the pool, estimated by SDS-PAGE, was greater than 90% as judged by visual inspection of gels after SDS-PAGE with Coomassie blue staining. Total protein in the pool, measured by the method of Bradford (Anal. Biochem., supra) using BSA as standard, was about 8 mg. Inhibitory activity of this material was demonstrated in several ways (Example 10).

A sample of this human MI preparation (about 6.5 μg) was subjected to amino-terminal amino acid sequencing through 18 cycles, using the methods described in Example 2. The initial yield was 135 pmol and the repetitive yield was 94%. The major sequence obtained exactly matched that predicted from the nucleotide sequence for the mature human MI gene (Example 3; FIG. 2).

The material is purified to apparent homogeneity using methods such as that described in Example 1 for bovine MI or other methods evident to those skilled in the art.

Example 6

Generation of Rabbit Polyclonal Antisera to Human Metalloproteinase Inhibitor

Two types of preparation of metalloproteinase inhibitor were used for generation of rabbit polyclonal antisera. The first (used for injections on days 1, 7 and 21) was prepared as follows. About 14 g (wet weight) of cell paste from *E. coli* strain FM5 harboring plasmid p1156 HMI2 (Example 3) was suspended in 50 ml $H_2O$ and passed twice through a French Press device. The pellet fraction obtained by centrifugation was resuspended in a final volume of 10 ml containing sodium sarkosyl (2%, w/v), Tris-HCl (50 mM), dithiothreitol (50 mM) with pH of 8.5, and incubated at 50° C. for 10-15 min and room temperature for 2 h, for solubilization of MI. After centrifugation of this mixture, a supernatant fraction (7.2 ml) containing MI was obtained and subjected to gel filtration on a Sephacryl S-200 column (265 ml column volume) equilibrated in 20 mM Tris-HCl, 1% (w/v) sodium sarkosyl, pH 8. Fractions of 2.9 ml were collected at a flow rate of 14 ml/h. Fractions 65-75 (31 ml) containing MI [as judged by SDS-PAGE with silver-staining; aliquots (0.5 μl; reduced) of fractions were run on gels containing 12.5% (w/v) acrylamide], were pooled, dialyzed thoroughly against 20 mM Tris-HCl, pH 8, concentrated to 6.5 ml using an Amicon stirred cell (with YM10 membrane), and filtered through a 0.45 p filter. The MI concentration in this preparation was about 1 mg/ml. The second type of preparation (used for injections on days 35 and 56) was that of Example 4, with MI at a concentration of 0.4-0.5 mg/ml.

The MI preparations were injected into 3 New Zealand white rabbits (5-8 lb. initial weight). Each rabbit was immunized on day 1 with 0.2 mg MI emulsified in an equal volume of Freund's complete adjuvant. A total volume of not more than 2 ml (1:1, MI:adjuvant) per rabbit was injected subcutaneously in at least 6 sites along the hindquarters. Further boosts (days 7, 21, 35 and 56) were performed by the same procedure, with the substitution of Freund's incomplete adjuvant.

Rabbits were bled by ear vein puncture on the day before the first injection (preimmune serum) and on days 28 and 63. Blood was collected into vacuum tubes and allowed to clot for 16 hours at room temperature. The clot was removed and the serum spun for 10 minutes at 2200 rpm to remove any remaining red blood cells. Serum, with sodium azide added to a final concentration of 0.01% (w/v), was stored at −20° C.

Serum was titered using a solid-phase radioimmunoassay; see Tsu et al., "Solid Phase Radioimmunoassays", pp. 373-397 in *Selected Methods in Cellular Immunology*, B. B. Mishel and S. M. Shiigi, eds., Freeman, San Francisco (1980), and *Hybridoma Technology in the Biosciences and Medicine*, Timothy A. Springer, ed., Plenum Press (1985), pp. 29-36. Metalloproteinase inhibitor was diluted to 0.5 μg/50 ul in carbonate-bicarbonate buffer, pH 9.2 and incubated for 2 h at room temperature in polystyrene wells (50 ul/well). Antigen solution was decanted; wells were then filled with 5% (w/v) BSA for 30 minutes at room temperature to block remaining binding sites on plastic. Dilutions of rabbit serum in PBS containing 1% (w/v) BSA were added to wells (50 ul/well) after the 5% (w/v) BSA was decanted. Incubations were carried out for 2 h at room temperature, then wells were washed with an imidazole-buffered saline containing 0.02% (w/v) Tween 20. $^{125}$I-Labeled protein A (100,000 cpm/50 ul) was added to wells and incubation was carried out for 30 min at room temperature, followed by a second wash. Wells were snapped apart and counted in a gamma counter. Cpm values were graphed against antiserum dilution to determine 50% titer (the dilution at which the antiserum binds half of the maximum counts bound). Sera obtained from the day 28 bleeds had titers ranging from 1:200 to 1:2500. Sera obtained from the day 63 bleeds had titers ranging from 1:800 to 1:4500.

These antisera were also used for SDS-PAGE with immunoblotting. As indicated in Examples 8 and 9, the antibody recognized a protein band of the expected $M_r$ in preparations of bovine MI, *E. coli-expressed* recombinant human MI, and CHO cell-expressed recombinant human MI.

Example 7

Expression of Recombinant Human Metalloproteinase Inhibitor by Yeast Cells

The human MI gene was from pUC HMI (Example 3). The MI gene was isolated from pUC HMI as a 586 base pair (bp) PstI to StuI DNA fragment. A synthetic DNA linker with HindIII and PstI sticky ends was used to fuse the MI gene to the yeast MFα1 in the vector pUC119αG4 (FIG. 10A). The synthetic DNA linker was:

```
            AGCTTGGACAAGAGATGCA
     (HindIII) ACCTGTTCTCT (PstI)
```

The vector pUC119αG4 contains a yeast glyceraldehyde-3-phosphate dehydrogenase promoter (GPD-P) followed by the pre-pro sequence (αF-s) and the transcription termination sequence (αF-t) of yeast mating factor α.

The vector pUC119αG4, in detail, consists of the following (see FIG. 10A):
I. pUC119 with deletion of HindIII, SalI, SstI and SmaI sites: pUC119 was digested with HindIII plus SalI, followed by S1 nuclease treatment to generate blunt ends, then ligation. The resulting plasmid was further digested with SstI plus SmaI, followed by S1 nuclease treatment, then ligation, resulting in deletion of HindIII, SalI, SstI and SmaI sites. An expression casette was then introduced into the remaining unique BamHI site.

II. The expression casette consists of the following:

(i) a 675 bp HindIII to BamHI fragment containing the yeast glyceraldehyde-3-phosphate dehydrogenase promoter (GPD-P) [Bitter et al., Gene 32, 263-278 (1984)], where the HindIII site was removed and a BamHI site was added. This was accomplished by digestion with HindIII followed by end-filling with the Klenow fragment of DNA polymerase I. The DNA fragment containing the end-filled HindIII site was blunt-end ligated into the SmaI site of pUC19.

```
(ii) A GPD-α-factor linker
(Sau3A)                  met arg phe pro ser ile phe thr ala
GATCACACATAAATAAACAAAATG AGA TTT CCT TCA ATT TTT ACT GCA TGTGTATTTATTTGTTTTAC TCT AAA GGA AGT TAA AAA TG (PstI)
```

(iii) A 218 bp PstI to HindIII fragment containing the α-factor pre-pro leader sequence from paC3 [Zsebo et al., J. Biol. Chem. 261, 5858-5865 (1986); Bitter et al., Methods in Enzymol. 153, 516-544 (1987)].
(iv) A linker for joining the α-factor pre-pro leader to the α-factor terminator sequence such as:

(v) An α-factor terminator sequence on an approximately 250 bp SalI to BamHI fragment from paC3, with the SalI site being destroyed after joining to the linker in (iv).

The α-factor-MI gene fusion was accomplished by digesting pUC119αG4 with HindIII and SmaI followed by ligation with the synthetic DNA linker and the MI DNA fragment. The resultant plasmid pUC119αG4-HMI depicted in FIG. 10A contains a yeast glyceraldehyde phosphate dehydrogenase promoter (GPD-P) followed successively by the α-factor pre-pro leader from the yeast MFα1 gene, the synthetic DNA linker above, the human metalloproteinase inhibitor gene DNA segment and α-factor transcription terminator. The 1800 bp BamHI DNA fragment containing the elements above was isolated from pUC119αG4 by a partial digest with BamHI and inserted into the BamHI site of the yeast-*E. coli* shuttle vector pYE3 resulting in the plasmid pYE3αG4-HMI (FIG. 10C).

The plasmid pYe3 is shown in FIG. 10B and consists of the following:
I. Yeast 2µ (B form) plasmid in pGT41 [Tschumper et al., Gene 23, 221-232 (1983)] where the 2500 bp BamHI to SalI LEU 2 gene segment was deleted by digestion with BamHI plus SalI, and this treatment was followed by mungbean nuclease treatment to generate blunt ends, followed by ligation.
II. A polylinker, whose sequence is shown below, was inserted into a EcoRI site of the modified 2µ plasmid in (I) as shown in FIG. 10B.

```
AATTC GATATC GAT GGTACC CGG GATCC GTCGAC AGATCT G
    G CTATAG CTA CCATGG GCC CTAGG CAGCTG TCTAGA CTTAA
EcoRI EcoRV ClaI KpnI SmaI BamHI SalI  BglII   EcoRI
```

EcoRI EcoRV ClaI KpnI SmaI BamHI SalI BglII EcoRI
III. A 852 bp BglII to EcoRI fragment containing the TRP 1 gene [Tschumper et al. Gene 10, 157-166 (1980)] inserted into the BglII and EcoRI sites of the polylinker in (II).

The plasmid pYE3αG4-HMI was grown in *E. coli* strain DH5α, the plasmid DNA was isolated and the DNA was transformed into the *S. cerevisiae* yeast strain EG45°. Other yeast host cells can also be used as will be apparent to those skilled in the art.

The strain EG45° (supra) was a mutant of the yeast strain SE7-6. The strain SE7-6 (Matα, trp1 deletion, pep4-3, GAL, cup1) was constructed using standard yeast genetic techniques. It was derived from crosses of several yeast strains including: (1) YSDP4 (ATCC 20734) which contains a mutation in the PEP4 gene; (2) a strain with an ability to grow on galactose [BWG1-7A obtained from L. Guarente, see Guarente et al., Proc. Natl. Acad. Sci. USA 79, 7410-7414 (1982) and Cell 36, 503-511 (1984)]; (3) a strain with a deletion of the TRP1 gene (YNN282 Yeast Genetic Stock Center, Berkeley, Calif.); and (4) a strain with sensitivity to copper (x36567D Yeast Genetic Stock Center, Berkeley,

```
HindIII SphI SstI SmaI XhoI BglII                    (SalI)
AGCTTGCATGCGAGCTCCCCGGGCTCGAGATCTGATAACAACAGTGTAGATGTAACAAAA

ACGTACGCTCGAGGGGCCCGAGCTCTAGACTATTGTTGTCACATCTACATTGTTTTAGCT
```

Calif.). The selection of SE7-6 was made based on its ability to grow on galactose and to secrete heterologous proteins efficiently.

Figure 11:
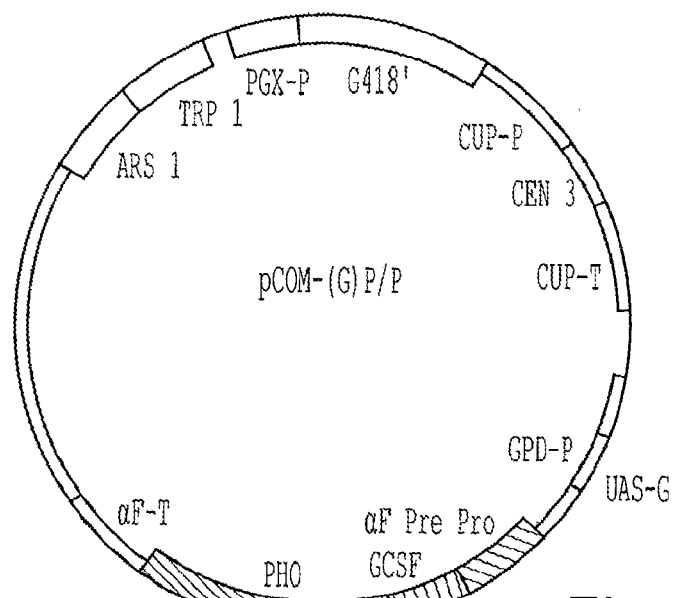
FIG. 11 shows vectors used for isolation of yeast secretion mutants.

To isolate EG45°, the strain SE7-6 was transformed with the plasmid pCOM(G)P/P. The plasmid pCOM(G)P/P contains an amplifiable copy number system (FIG. 11). It can be transformed into yeast trp1 cells by selection for tryptophan prototrophy via the TRP1 ARS1 yeast DNA segment (see Bitter et al., Methods Enzymol., supra). Under normal conditions the plasmid is stable at a copy number of one per cell. Growth on copper-containing medium induces transcription from the CUP promoter (CUP-P) which inhibits centromere (CEN3) function. CUP-T is the CUP terminator region. Therefore copy number increases and plasmid stability decreases. Following removal of copper the plasmids stabilize. Normally the copy number returns to one per cell; however selection for G418 resistance via the Tn5 gene [Jiminez et al. Nature 287, 869-871 (1980)] [controlled by the yeast PGK promoter (PGK-P)] results in cells containing 5-10 copies of plasmid per cell which are stably maintained.

Transformation of EG45° was done by electroporation of plasmid DNA into yeast cells at 900 volts for 5 milliseconds at 25 microfarads in a Bio-Rad gene pulser. Electroporated cells were plated on SD-CAA agar which contains 6.7 g/L yeast nitrogen base without amino acids (Difco), 2% (w/v) glucose, 0.5% (w/v) casamino acids (Difco) and 2% (w/v) agar, and transformed cells were obtained by growth at 30° C.

The transformed cells were grown in a 15 L fermentor using fed-batch fermentation. The medium composition is shown below:

| Chemicals | Batch medium | Feed medium |
| --- | --- | --- |
| Casamino acids | 25 g/L | 125 g/L |
| Yeast extract | 5 g/L | 10 g/L |
| $(NH_4)_2PO_4$ | 3.8 g/L | 5 g/L |
| $KH_2PO_4$ | 13.5 g/L | 2.8 g/L |
| Glucose | 2 g/L | 533 g/L |
| Inositol | 0.02 g/L | 0.03 g/L |
| $MgSO_4 \cdot H_2O$ (1 M) | 4 ml/L | 15 ml/L |
| Trace metal solution[a] | 3 ml/L | 6.6 ml/L |
| Vitamin solution[a] | 3 ml/L | 6.6 ml/L |
| Streptomycin sulfate | 0.23 g/L | |
| Thiamine (10 g/100 ml) | 0.6 ml/L | 1.6 ml/L |

[a]Trace metal solution and vitamin solution were the same as described by Tsai et al., J. Industrial. Microbiol. 2, 181-187 (1987).

The pH of the medium was maintained at 6.0 and the temperature at 25° C. Dissolved oxygen was controlled by aeration, back pressure and agitation. Cells were grown to $OD_{600}$ of 85-95.

Example 8

Characterization of Yeast-Secreted Recombinant Human Metalloproteinase Inhibitor Culture medium containing yeast-expressed recombinant human MI was harvested by centrifugation to remove the cell paste. The supernatant fraction was subjected to SDS-PAGE (reducing conditions) with silver-staining. A band migrating with $M_r$ of about 26,000 (24,000-28,000) was observed for supernatants produced by yeast (strain EG45°) transformants containing pYE3αG4-HMI. The polypeptide represented by this band was present at about 25 to 50 mg per liter of supernatant. The $M_r$ 26,000 band was not observed in control fermentor supernatants. The $M_r$ 26,000 band had the same mobility on SDS-PAGE as MI purified from bovine endothelial cell conditioned medium (Example 1). By DS-PAGE with silver-staining performed on aliquots (10 µl) of MI-containing yeast supernatants in unreduced conditions, the $M_r$ 26,000 band was absent, and there was instead an $M_r$ 22,000-23,000 band. Material represented by the $M_r$ 22,000-23,000 band was present at about 2-5 mg per liter of supernatant, and was not seen in control supernatants. To demonstrate that the $M_r$ 26,000 (reduced) and $M_r$ 22,000-23,000 (unreduced) bands represented human MI, a polyclonal antibody raised in rabbits against human MI produced in E. coli (Example 6) was used. SDS-PAGE with immunoblotting (Burnette, Anal. Biochem., supra) was performed using this antibody preparation and a Vectastain ABC kit (Vector laboratories) containing biotinylated anti-rabbit immunoglobulin, avidin, and biotinylated horseradish peroxidase. Immunoreactive bands were seen for supernatants from the yeast strain transfected with the MI gene-containing plasmid (10 µl loaded) and not for control supernatants. [$M_r$ 26,000 and $M_r$ 18,000 bands were present for reduced samples and $M_r$ 22,000-23,000 band for unreduced samples. The $M_r$ 18,000 (reduced) band is presumed to be a proteolytic breakdown fragment of MI.] The antibody also reacted in immunoblots with MI purified from bovine enthothelial cell conditioned medium (350 mU) and with E. coli-produced human MI (0.3 µg) which indicates that the bands observed in yeast supernatants did in fact represent human MI.

Example 9

Expression of Human Metalloproteinase Inhibitor in Chinese Hamster Ovary Cells

1. Construction of an Expression Vector.

To generate expression plasmids, the NcoI to EcoRI fragment of pUC HMI (Example 3) containing the intact coding sequence of human MI [including the sequence coding for the 26-amino acid leader FIG. 2)] was first subcloned into pCFM 1156, from the NcoI to the EcoRI restriction site to give plasmid p1156 HMINR. The plasmid pCFM 1156 was derived from plasmid pCFM 836 (see U.S. Pat. No. 4,710,473 hereby incorporated by reference), by destroying the two endogenous NdeI restriction sites, end filling with T4 DNA polymerase followed by blunt end ligation and substituting the small DNA sequence between the unique ClaI and KpnI restriction sites with the following oligonucleotide:

```
         ClaI                                                         KpnI
    5'   CGATTTGATTCTAGAAGGAGGAATAACATATGGTTAACGCGTTGGAATTCGGTAC    3'

3'        TAAACTAAGATCTTCCTCCTTATTGTATACCAATTGCGCAACCTTAAGC    5'
```

The human MI cDNA was retrieved from plasmid p1156 HMINR as a 0.65 kb HindIII to StuI fragment. This fragment was then cloned into the expression vector pDSRα2 to generate plasmid pDSFα2-MI.

Figure 12:
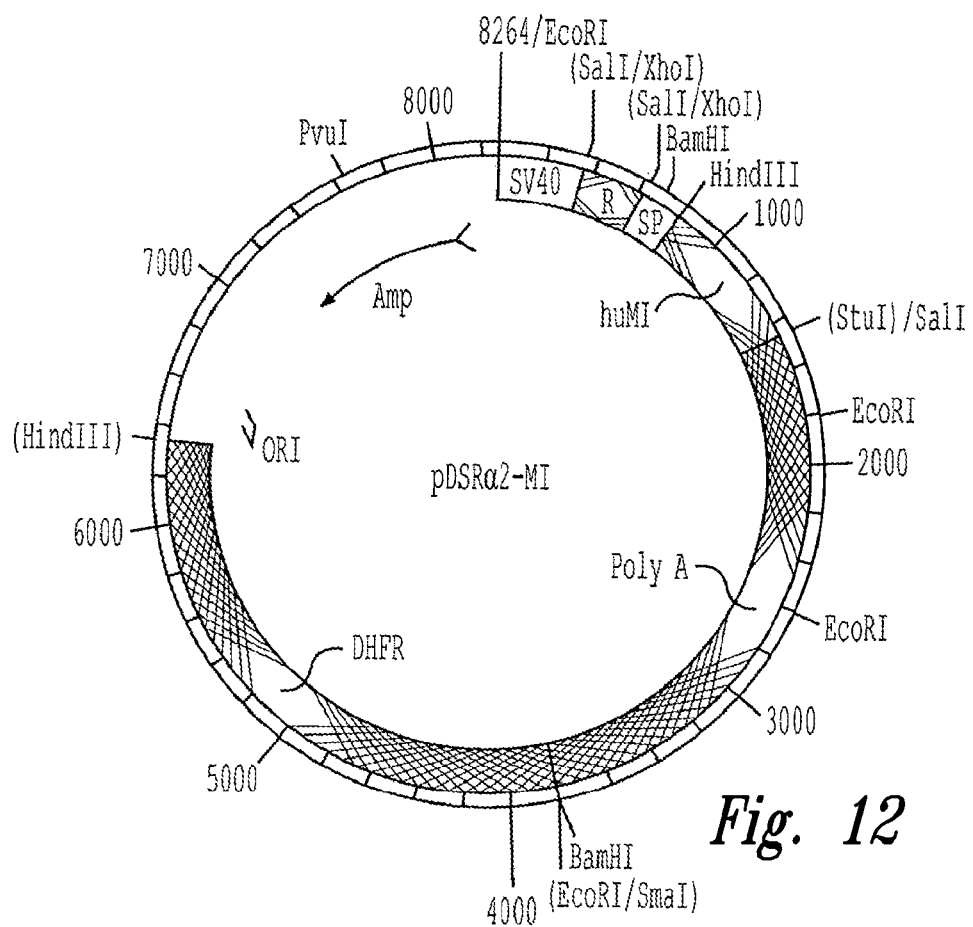
FIG. 12 shows the structure of mammalian cell expression vector pDSRα2-MI.

Plasmid pDSRα2 has the following important features (following the map in FIG. 12 in a clockwise direction):
(a) SV40 early promoter/enhancer and origin of replication; composed of SV40 sequences between PvuII (SV40 nucleotide map coordinate #272) and HindIII (map coordinate #5172) sites. [*DNA Tumor Viruses*, J. Tooze, ed., Cold Spring Harbor Laboratories, Cold Spring Harbor, N.Y. (1981), pp. 801-804].
(b) A 267 bp fragment containing the "R" element and part of the "U5" sequences of the long terminal repeat (LTR) of human T-cell leukemia virus type 1 (HTLV-1). This fragment maps at the exact 5' end of "R" (position 354) to the Sau3A site in the U5 sequences (position 620) [Seiki et al. Proc. Natl. Acad. Sci. USA 80, 3618-3622 (1983)].
(c) A fragment composed of SV40 16S, 19S splice donor/acceptor signals (map coordinates #502-560 and #1410-1498 joined by an BamHI linker).

The structural organization of the above three segments (a), (b) and (c) is identical to the published vector pCD-SRα [Takebe et al., Mol. Cell. Biol. 8, 466-472 (1988)] with the following modifications: (1) at the 5' end of segment (a), the HindIII site has been destroyed by end-filled ligation done with the Klenow fragment of DNA polymerase I; (2) the original XhoI site between segments (a) and (c) has been destroyed through the insertion of segment (b); (3) at the 3' end of the (c) segment, the original PstI site was changed into a HindIII site.
(d) A transcription termination/polyadenylation signal residing on a SalI to BamHI fragment of 2.4 kb. This fragment was obtained from the 3' portion of the α-subunit of bovine pituitary glycoprotein hormone α-FSH (folicle stimulating hormone). A BstXI site at the beginning of the last exon was mutagenized to a SalI site. The 3' end of the fragment continued to the nearest downstream BamHI site. This 2.4 kb fragment was subcloned into a pUC vector and then retrieved as a SalI to SmaI fragment for further construction of the expression vector.
(e) A mouse dihydrofolate reductase (DHFR) minigene containing the endogenous mouse DHFR promoter, the cDNA coding sequences, and the DHFR transcription termination/polyadenylation signals all as an EcoRI to HindIII fragment of 2.5 kb, retrieved initially from plasmid pMg 1 [Gasser et al., Proc. Natl. Acad. Sci. USA 79, 6522-6526 (1982)]. Both of the terminal restriction endonuclease sites, i.e., the 5' EcoRI and the 3' HindIII, were destroyed upon construction of the expression vector.
(f) The "poisonless" pBR322 sequences extending from the HindIII site (map coordinate #2448) to EcoRI site (map coordinate #4362) and containing the ampicillin resistance marker gene and the origin for replication of the plasmid in *E. coli*.

Through multiple steps of subcloning, these six segments of DNA [(a)-(f)] were finally ligated to generate the expression vector pDSRα2; several of the original restriction endonuclease cleavage sites were destroyed or altered during the process. The final structure of the plasmid pDSRα2-MI is thus illustrated in FIG. 12 in its circular configuration with these changes clearly depicted.

2. Transfection Conditions.

DHFR-deficient (DHFR$^-$) Chinese hamster ovary (CHO) cells [Chasin & Urlaub, Proc. Natl. Acad. Sci. USA 77, 4216-4280 (1980)] were maintained routinely in Dulbecco Modified Eagle's Medium supplemented with 5% (v/v) fetal bovine serum (FBS), L-glutamine (292 μg/ml), non-essential amino acids (100 μM), hypoxanthine (13.6 μg/ml), thymidine (7.6 μg/ml), penicillin (100 U/ml) and streptomycin sulfate (100 μg/ml).

One million cells (plated on a 60 mm dish one day prior to transfection) were transfected separately with 20 μg of pDSRα2-MI11 or pDSRα2-MI14 (two independently isolated plasmids) plasmid DNA by a modified calcium phosphate precipitation method [Chen et al., Mol. Cell. Biol. 7, 2745-2752 (1987)]. Three days post-transfection, the cells were split to eight 100 mm dishes. At this point, medium lacking hypoxanthine and thymidine, and containing 10% (v/v) dialyzed FBS, was used for the selection of transfectants. Medium was changed every 2-3 days to ensure the selection. At the end of the second week after transfection, twenty-four stable transfectants were selected from each set of dishes for analysis for transcription and translation of the MI gene.

3. Analysis for mRNA Transcribed from the Recombinant Human MI Gene.

Total cytoplasmic RNA from transfected CHO cells was prepared as described in Resendez et al. [J. Cell Biol. 103, 2145-2152 (1986)]. Cellular RNA (7.5 μg) was separated by 1% formaldehyde-formamide denaturing agarose gel electrophoresis and transferred onto a GeneScreen Plus membrane. Radiolabeled HindIII to PvuI fragment of pDSRα2-MI11 was used to identify the human MI transcript using the hybridization conditions described by Lin et al. [Gene 44, 201-209 (1986)]. A single RNA band was observed in four of the seven individual stable clones analyzed. The size of the message was 1.5 kb as expected from the construct.

4. Protein Analysis and Quantitation.

Recombinant human MI was identified and quantitated by SDS-PAGE with immuno-blotting with antibody against human MI as described in Example 8. Conditioned media from stable transfected clones (serum-free; 10-50 μl aliquots) were analyzed. Results indicated that transfected CHO cells secrete a $M_r$ 26,000 (24,000-28,000) (reduced) protein which can be recognized by the antibody. This protein co-migrates with the *E. coli*-produced recombinant human MI. The transfectant with highest MI expression produced about 1 mg/liter/day on a confluent 100 mm tissue culture dish without amplification.

5. Bioactivity Assay.

Activity could be detected in transfected CHO cell supernatants by the type I collagenase inhibition assay described in Example 1. Results are given in Example 10.

Example 10

Demonstration of Inhibitory Activity in Recombinant Human MI Samples

1. *E. coli*-Expressed Recombinant Human MI.

Human MI from *E. coli*, prepared as described in Example 4, had inhibitory activity of about 424 U/ml (specific activity about 865 U/mg) measured by the type I collagenase inhibition assay described in Example 1, section 2).

Figure 13:
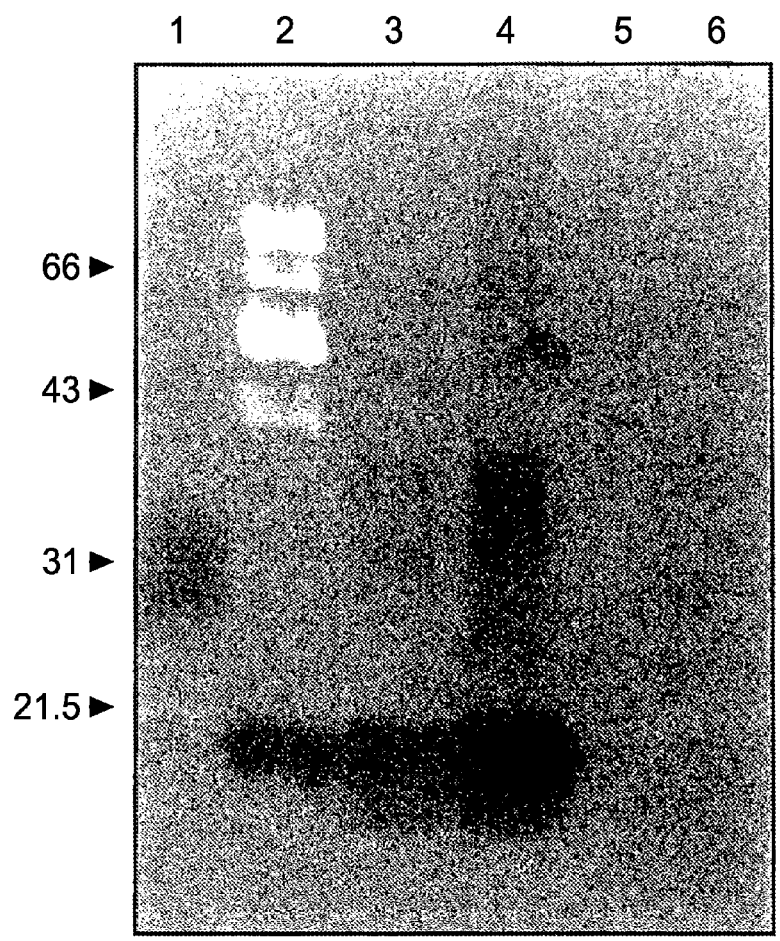
FIG. 13 shows SDS-gelatin PAGE for bovine metalloproteinase inhibitors and for recombinant human metalloproteinase inhibitor (MI) produced in *E. coli*.

This preparation was also analyzed by SDS-gelatin PAGE (FIG. 13; method as described in Example 1, section 4b). The legend to FIG. 13 is as follows (all samples were unreduced):
Lane 1, peak II-derived inhibitor from bovine endothelial cells (24 mU);
Lane 2, peak I-derived inhibitor (MI) from bovine endothelial cells (50 mU);
Lane 3, human MI prepared from *E. coli* (Example 4; 92 mU);

Lane 4, human MI preparation from *E. coli* (Example 4; 420 mU);

Lane 5 and 6, buffer only lanes.

Noting the dark zones in lanes 1-4, it is apparent that all of the indicated inhibitor preparations, including the recombinant preparations from *E. coli*, have proteins of the expected molecular weights with inhibitory activity as judged by this method.

Figure 14:
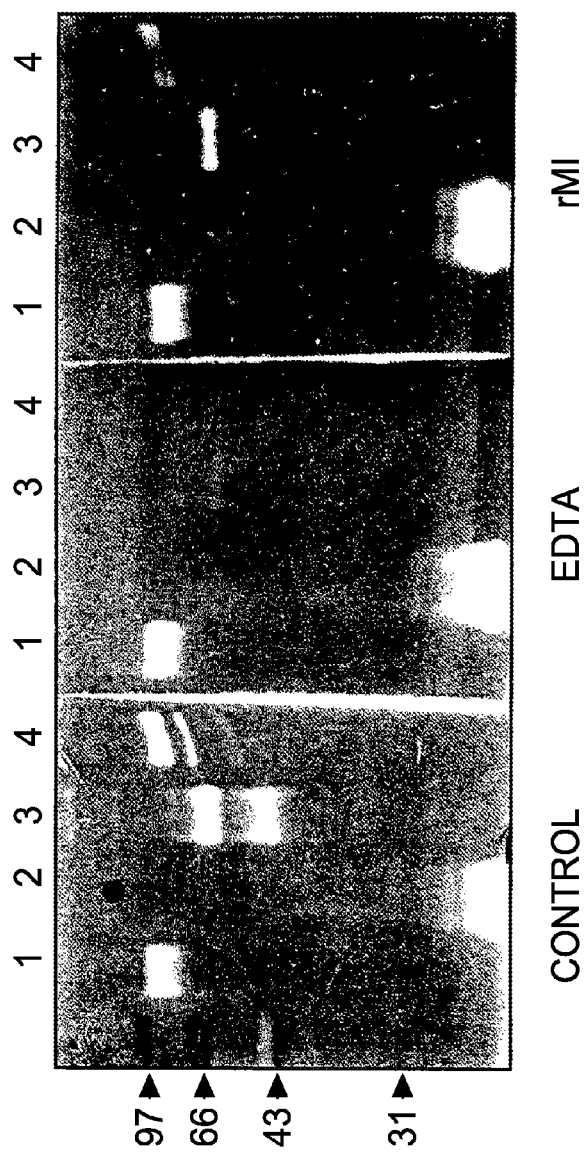
FIG. 14 shows effect of EDTA and of *E. coli*-produced recombinant human metalloproteinase inhibitor (MI) on gelatinolytic proteinase run on SDS-gelatin PAGE.

The method of SDS-gelatin PAGE with proteinases as samples (Example 1, section 4c) was also used to analyze the *E. coli*-produced recombinant human MI (FIG. 14). In FIG. 14, lanes marked "control" were incubated overnight with no inhibitor additions; lanes marked "EDTA" were incubated with 20 mM EDTA present; lanes marked "rMI" were incubated with *E. coli*-produced human MI (preparation of Example 4, 423 mU/ml). The samples electrophoresed prior to the overnight incubations were: lanes 1, human plasmin, 50 μg; lanes 2, bovine trypsin, 0.3 μg; lanes 3, 5 μl of 100-fold concentrated conditioned medium from metastatic tumor cells [c-Ha-ras-transfected rat embryo fibroblasts, as source of type IV collagenase; conditioned medium prepared according to Garbisa et al., Canc. Res. 47, 1523-1528 (1987)]; lanes 4, APMA-activated conditioned medium from TPA-treated rabbit synovial fibroblasts (4 mU of collagenase I activity loaded; see Example 1, section 2). It is apparent that the recombinant MI inhibits the type I and type IV collagenases, but does not inhibit plasmin and trypsin (which are not metalloproteinases). EDTA also inhibits the collagenases, as expected.

The recombinant human MI from *E. coli* also inhibited the specific collagen cleavage characteristic of mammalian collagenases (see Example 1 and FIG. 7). Experiments showing this were done essentially as described for FIG. 7 in Example 1, using the recombinant human MI at about 2 μg/ml in the incubations. Results were equivalent to those shown in FIG. 7 for the bovine MI from endothelial cells.

2. CHO Cell-Expressed Recombinant Human MI.

A pool (about 2×10$^6$ cells plated) derived from colonies of pDSRα2-MI11-transfected CHO cells (Example 9, Section 2) was grown serum-free and the conditioned medium harvested. Inhibitory activity of 6.9 U/ml was measured by the type I collagenase inhibition assay described in Example 1, section 2, compared with 0.7 U/ml for serum-free medium conditioned by control cells.

3. From the data of sections 1 and 2 of this Example, and from the SDS-PAGE with immunoblot analyses done on bovine MI, yeast-expressed recombinant human MI, and CHO cell-expressed recombinant human MI using polyclonal antibody against *E. coli-produced* human MI (see Examples 6, 8 and 9), it is definitively proved that the isolated/cloned bovine and human genes described in Example 3 do in fact represent genes for MI.

While the present invention has been described in terms of preferred embodiments, it is understood that variations and modifications will occur to those skilled in the art. Therefore, it is intended that the appended claims cover all such equivalent variations which come within the scope of the invention as claimed.

What is claimed is:

1. A purified and isolated metalloproteinase inhibitor comprising a polypeptide, wherein said polypeptide;
   (a) has as a mature protein, an amino terminal amino acid sequence comprising at least the amino acid residues 1 to 42 of FIG. 2, and
   (b) has at least one biological activity of naturally occurring human metalloproteinase inhibitor, said biological activity selected from the group consisting of in vitro metalloproteinase inhibitor activity and immunological activity.

2. A polypeptide according to claim 1, wherein said polypeptide is the product of procaryotic or eucaryotic expression of an exogenous DNA sequence.

3. A polypeptide according to claim 1 further characterized by being free of association with any mammalian protein.

4. A polypeptide according to claim 2, wherein the exogenous DNA sequence is a cDNA sequence.

5. A polypeptide according to claim 2, wherein the exogenous DNA sequence is carried on an autonomously replicating DNA plasmid or viral vector.

6. A polypeptide according to claim 1, wherein said biological activity of naturally-occurring metalloproteinase inhibitor is immunological activity.

7. A polypeptide according to claim 1, wherein said biological activity of naturally-occurring metalloproteinase inhibitor is in vitro metalloproteinase inhibitor activity.

8. A polypeptide according to claim 1, further characterized by being covalently associated with a detectable label substance.

9. A synthetic polypeptide having part of all of the amino acid sequence as set forth in FIG. 2 and having one or more of the in vitro biological activities of naturally-occurring metalloproteinase inhibitor.

10. A synthetic polypeptide having part or all of the secondary conformation of part or all of the amino acid sequence set forth in FIG. 2 and having a biological property of naturally-occurring human metalloproteinase inhibitor.

11. Purified and isolated human metalloproteinase inhibitor according to claim 1 in glycosylated or nonglycosylated form free of association with any human protein.

12. A pharmaceutical composition comprising an effective amount of a polypeptide according to claim 1 and a pharmaceutically acceptable diluent, adjuvant, or carrier.

13. A polypeptide according to claim 6, wherein said immunological activity is an ability to react with rabbit polyclonal antisera raised against human metalloproteinase inhibitor.

14. A polypeptide according to claim 7, wherein said in vitro biological activity is an ability to inhibit collagenase.

15. A polypeptide according to claim 14, wherein said collagenase is type 1 collagenase.

* * * * *